United States Patent
Nomura

(10) Patent No.: US 8,486,010 B2
(45) Date of Patent: Jul. 16, 2013

(54) BENDABLE CATHETER

(75) Inventor: Yusuke Nomura, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/440,303

(22) Filed: Apr. 5, 2012

(65) Prior Publication Data

US 2012/0265132 A1 Oct. 18, 2012

Related U.S. Application Data

(63) Continuation of application No. PCT/JP2011/067849, filed on Aug. 4, 2011.

(60) Provisional application No. 61/385,727, filed on Sep. 23, 2010.

(51) Int. Cl.
*A61M 31/00* (2006.01)

(52) U.S. Cl.
USPC .............. 604/95.04; 604/103.09; 604/526

(58) Field of Classification Search
CPC .................................................. A61M 31/00
USPC .............. 604/95.04, 103.09, 526, 528
See application file for complete search history.

(56) References Cited

U.S. PATENT DOCUMENTS

| | | | | |
|---|---|---|---|---|
| 5,820,591 A | * | 10/1998 | Thompson et al. | 604/95.01 |
| 6,053,903 A | * | 4/2000 | Samson | 604/526 |
| 6,139,510 A | * | 10/2000 | Palermo | 600/585 |
| 6,198,974 B1 | * | 3/2001 | Webster, Jr. | 607/122 |
| 6,346,099 B1 | * | 2/2002 | Altman | 604/528 |
| 6,511,462 B1 | * | 1/2003 | Itou et al. | 604/264 |
| 6,547,757 B1 | * | 4/2003 | Kranz et al. | 604/95.04 |
| 6,602,278 B1 | * | 8/2003 | Thompson et al. | 604/95.04 |
| 2002/0156459 A1 | | 10/2002 | Ye et al. | |
| 2003/0060802 A1 | * | 3/2003 | Omaleki et al. | 604/528 |

FOREIGN PATENT DOCUMENTS

| | | |
|---|---|---|
| JP | S57-148927 A | 9/1982 |
| JP | 8-24341 A | 1/1996 |
| JP | 11-48171 A | 2/1999 |
| JP | 2000-70269 A | 3/2000 |
| JP | 2000-308684 A | 11/2000 |

(Continued)

OTHER PUBLICATIONS

Japanese Office Action dated May 29, 2012 received from related Japanese Patent Application No. 2012-517020, together with a partial English translation.

(Continued)

*Primary Examiner* — Laura Bouchelle
*Assistant Examiner* — Gerald Landry, II
(74) *Attorney, Agent, or Firm* — Scully, Scott, Murphy & Presser, P.C.

(57) ABSTRACT

The bendable catheter includes a flexible tubular main tube; a bendable part having a longitudinal axis and an internal space formed along the longitudinal axis, and being capable of being bent; a first coil provided in the internal space along the longitudinal axis; a second coil having a central axis extending parallel to a central axis of the first coil and provided adjacent to the first coil in a space formed between the bendable part and the first coil; and a bending manipulation wire arranged within the second coil, being capable of bending the bendable part, and having one end fixed to the bendable part.

16 Claims, 33 Drawing Sheets

FOREIGN PATENT DOCUMENTS

| | | |
|---|---|---|
| JP | 2001-9042 A | 1/2001 |
| JP | 2002-272675 A | 9/2002 |
| JP | 2005-501613 A | 1/2005 |
| JP | 2007-507305 A | 3/2007 |
| JP | 2008-502433 A | 1/2008 |
| WO | WO 2005/032639 A1 | 4/2005 |
| WO | WO 2005/123169 A1 | 12/2005 |
| WO | WO 2009/054509 A1 | 4/2009 |

OTHER PUBLICATIONS

International Search Report dated Oct. 25, 2011 from corresponding International Application No. PCT/JP2011/067849.

\* cited by examiner

BENDABLE CATHETER

This application is a Continuation Application of International Patent Application No. PCT/JP2011/067849, filed on Aug. 4, 2011, claiming priority based on U.S. Application No. 61/385,727, provisionally filed in the U.S. on Sep. 23, 2010, the contents of which are incorporated herein by reference in their entirety.

TECHNICAL FIELD

The present invention relates to a bendable catheter capable of being bent.

BACKGROUND ART

Previously, for example, endoscopic mucosal resection (EMR), endoscopic submucosal dissection (ESD), and the like are known as examples of procedures for performing treatment within lumen tissues. Additionally, as procedures for diagnosing abnormalities of the bile duct or the pancreatic duct, endoscopic retrograde cholangiopancreatography (ERCP) is known. In ERCP, an X-ray image can be taken by inserting a catheter via the papilla of the duodenum, and subsequently, directly injecting a contrast medium into the pancreatic duct or the bile duct (for example, refer to Japanese Patent Application, First Publication No. 2002-272675).

SUMMARY OF INVENTION

According to one aspect of the present invention, a bendable catheter is provided including: a flexible tubular main tube; a bendable part having a longitudinal axis and an internal space formed along the longitudinal axis, and being provided at a distal end of the main tube and capable of being bent; a first coil provided in the internal space along the longitudinal axis and having an external diameter smaller than an internal diameter of the bendable part; a second coil having central axis extending parallel to a central axis of the first coil and provided adjacent to the first coil in a space formed between the bendable part and the first coil; and a bending manipulation wire arranged so as to be movable along the longitudinal axis within the second coil, being capable of bending the bendable part according to movement thereof in a direction of the longitudinal axis, and having one end fixed to the bendable part.

In this case, the main tube may have a first lumen and a second lumen that open at a distal end and a proximal end of the main tube and that allow the distal end and the proximal end to communicate with each other. Additionally, the bendable part may have: a tubular bendable tube fixed to the distal end of the main tube and being more flexible than the main tube; the first coil having a distal end arranged within the bendable tube and a proximal end provided with an inner cavity communicating with the first lumen, and fixed to at least one of the main tube and the bendable tube; and the second coil fixed to an inner surface of the bendable tube. Additionally, the bending manipulation wire may be inserted through an inner cavity of the second coil and the second lumen, and a distal end of the bending manipulation wire may be fixed to at least one of the bendable tube, the first coil, and the second coil.

Additionally, a proximal end of the second coil may be closer to a distal end of the bendable catheter than both an opening at the distal end in the first lumen and an opening at the distal ends in the second lumen, and the first coil may be fixed to an inner wall surface of the first lumen.

Additionally, both the first coil and the second coil may be loosely wound.

Additionally, the main tube and the bendable tube may have light permeability.

Additionally, the main tube may include: a first tubular tube fixed to a proximal end of the first coil and having the first lumen formed therein; and a second tubular tube through which the first tube inserted and having the second lumen between the first tube and the second tube.

Additionally, the first coil may have a length in a direction of the central axis thereof longer than the second coil.

Additionally, the second coil may be exposed inside the bendable tube.

Additionally, an external surface of the second coil may be in contact with an external surface of the first coil.

Additionally, each loop of the second coil may enter between adjacent loops of the first coil, and a wire of the first coil and a wire of the second coil may be arranged alternately in a direction of the central axis of the first coil, in a portion where the second coil enters the first coil.

Additionally, a winding interval of a wire of the first coil and a winding interval of a wire of the second coil may be equal to each other.

Additionally, at least one of the first coil and the second coil may contain a material appearing on an X-ray transparent image.

Additionally, a distal end of the first coil and a distal end of the second coil may be fixed together by brazing, soldering, or welding.

Additionally, a distal end of the second coil and a distal end of the bending manipulation wire may be fixed together by brazing, soldering, or welding.

DESCRIPTION OF EMBODIMENTS

A bendable catheter 1 in an embodiment of the present invention will be described with reference to the drawings.

The bendable catheter 1 of the present embodiment is a tubular medical instrument to be used while being inserted into a patient's body.

Figure 1:
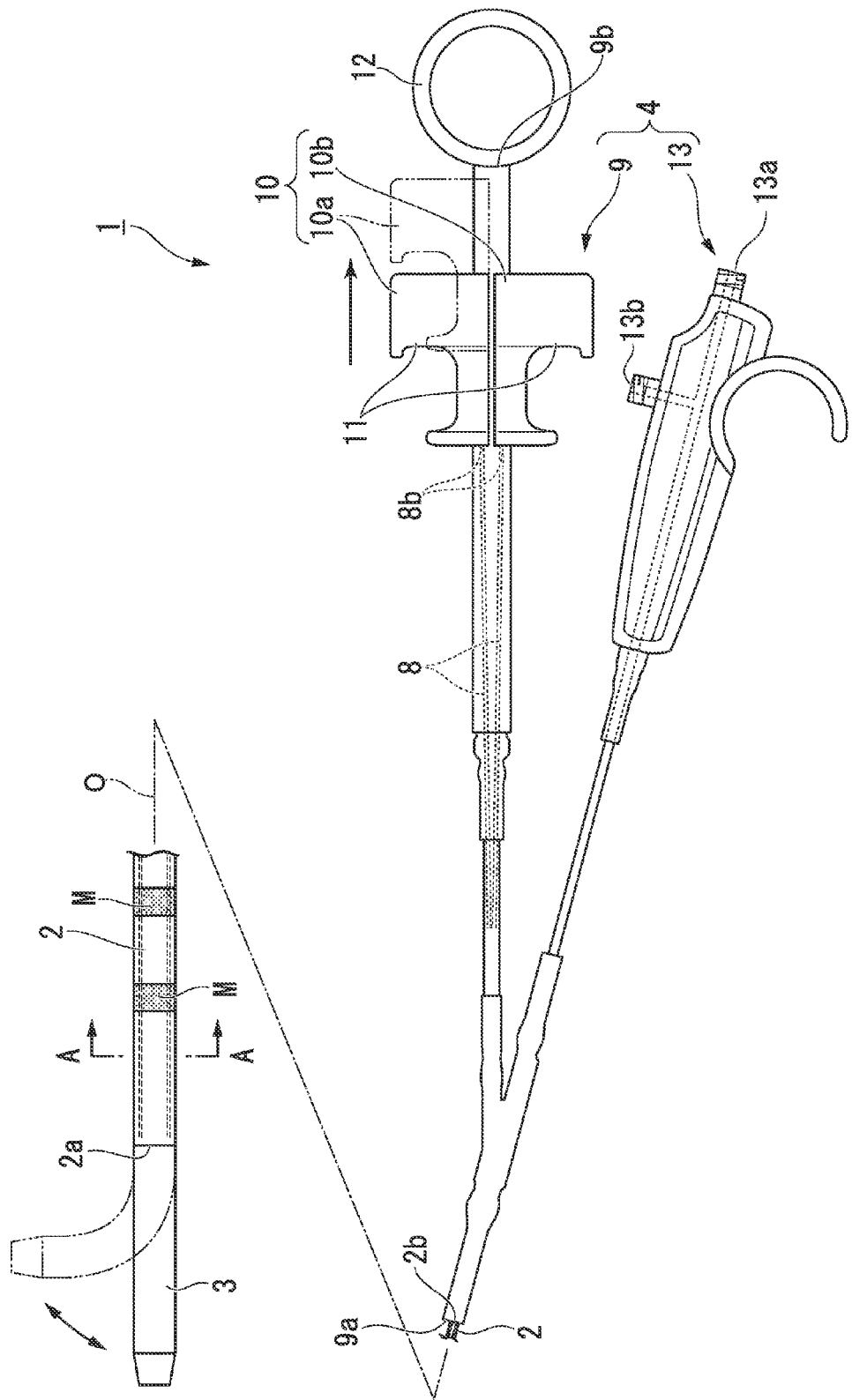
FIG. 1 is a view showing a bendable catheter in an embodiment of the present invention.

FIG. 1 is a view showing the bendable catheter 1. As shown in FIG. 1, the bendable catheter 1 includes a flexible tubular multi-lumen tube 2 (main tube) having a distal end 2a and a proximal end 2b, a bendable part 3 provided at the distal end of the multi-lumen tube 2 and capable of being bent, and a manipulating part 4 fixed to the proximal end of the multi-lumen tube 2. Hereinafter, in the bendable catheter 1, description will be made with the side where the bendable part 3 is provided being a distal end side in the bendable catheter 1 and the side where the manipulating part 4 is provided being a proximal end side in the bendable catheter 1.

Figure 2:
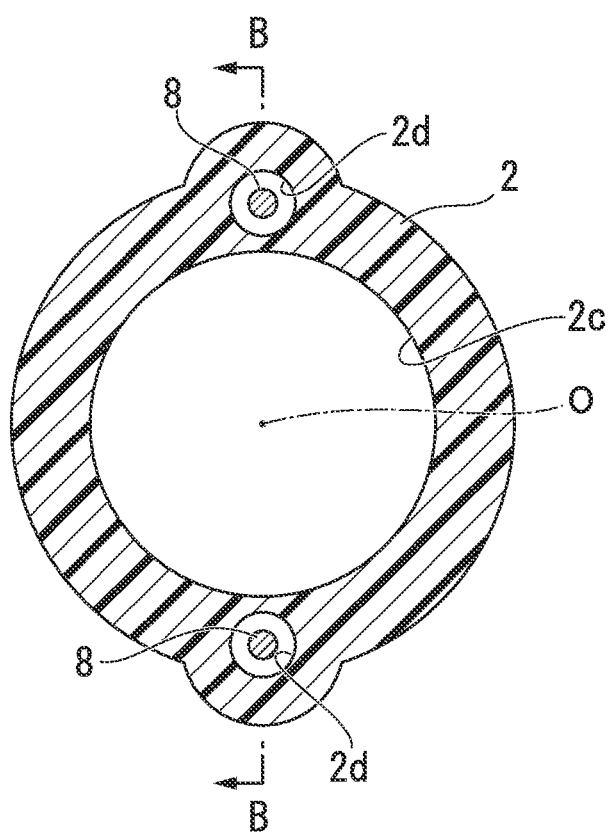
FIG. 2 is a cross-sectional view in a line A-A of FIG. 1.

FIG. 2 is a cross-sectional view in a line A-A of FIG. 1. As shown in FIG. 2, as seen in a section orthogonal to a central axis O of the multi-lumen tube 2 (hereinafter referred to as "radial section of the multi-lumen tube 2"), the shape of the outer periphery of the multi-lumen tube 2 is substantially circular, and is a shape in which two opposed portions protrude outward. A first lumen 2c and second lumens 2d that open to each of the distal end and proximal end of the multi-lumen tube 2 are formed inside the multi-lumen tube 2.

The first lumen 2c is a through-hole that has a circular shape centered on the central axis O of the multi-lumen tube 2 as a profile shape as seen in the radial section of the multi-lumen tube 2 and that is formed in the multi-lumen tube 2. The internal space of the first lumen 2c is used to pass a medical treatment tool, a medical guide wire for guiding the medical treatment tool in the body, or the like therethrough or to perform air supply, water supply, or suction. The internal space of the first lumen 2c is formed so as to allow the distal end and proximal end of the multi-lumen tube 2 to communicate with each other.

The second lumen 2d is a through-hole that is formed at each of two locations that oppose each other with the first lumen 2c interposed therebetween in the radial section of the multi-lumen tube 2. The second lumens 2d extend parallel to each other along the portions that protrude outward in the multi-lumen tube 2. The second lumens 2d are provided apart from the first lumen 2c in the radial direction thereof and adjacent to the first lumen 2c. As seen in the radial section of the multi-lumen tube 2, the profile shape of each second lumen 2d is a circular shape. The diameters of the second lumens 2c are equal to each other. The internal space of each second lumen 2c is formed so as to allow the distal end 2a and proximal end 2b of the multi-lumen tube 2 to communicate with each other. A bending manipulation wire 8 to be described below is inserted through the internal space of each second lumen 2d so as to be able to advance and retract.

As shown in FIG. 1, the outer peripheral surface of the multi-lumen tube 2 at the distal end 2a is provided with markings M made of a material appearing on an X-ray transparent image. The markings M are members that allow a manipulator to confirm the amount of insertion of the bendable catheter 1 inserted into a gap between body tissues or into a lumen within the body with reference to the X-ray transparent image.

As the material of the multi-lumen tube 2, a resin material having flexibility can be employed appropriately. Additionally, a bending tendency is suitably given to the distal end of the multi-lumen tube 2. For example, PEFE, polyethylene, or the like can be used as the material of the multi-lumen tube 2. In the present embodiment, the multi-lumen tube 2 has light permeability. This enables a medical treatment tool, a medical guide wire, or the like inserted into the first lumen 2c to be visually recognized from the outside of the multi-lumen tube 2.

Figure 3:
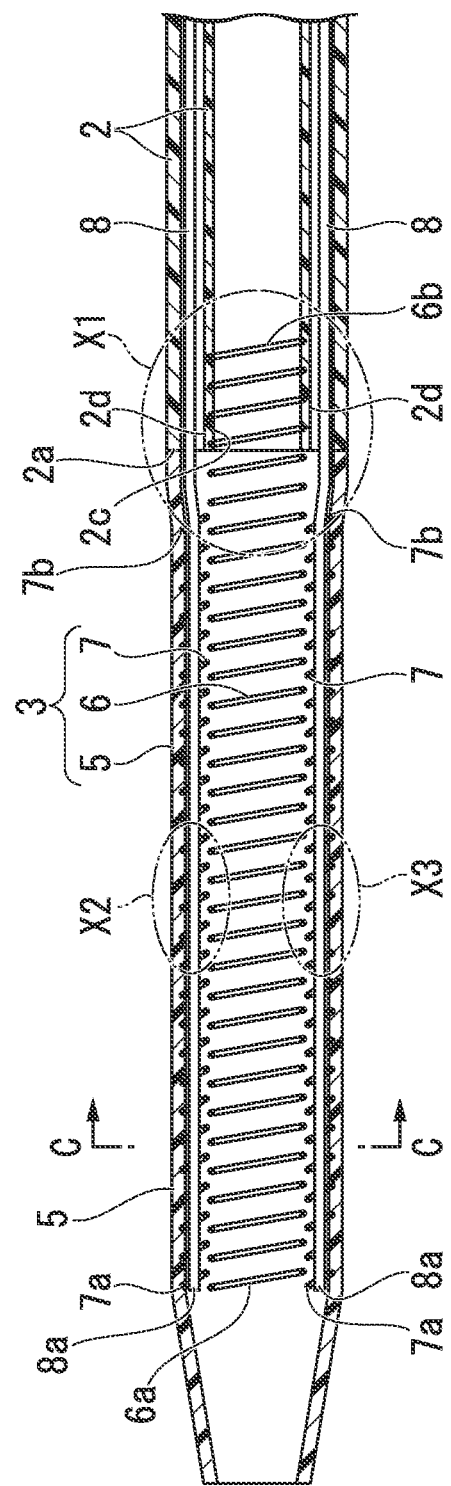
FIG. 3 is a cross-sectional view in a line B-B of FIG. 2.

FIG. 3 is a cross-sectional view in a line B-B of FIG. 2. As shown in FIG. 3, the bendable part 3 has a bendable tube 5, a first coil 6, and second coils 7.

The bendable tube 5 is a tubular member more flexible than the multi-lumen tube 2. The bendable tube 5 has the shape of a tube that opens at both ends thereof, and has one end (proximal end) fixed to the distal end of the multi-lumen tube 2 by heat welding. The bendable tube 5 and the multi-lumen tube 2 are arranged coaxially, and both the first lumen 2c and the second lumens 2d of the multi-lumen tube 2 communicate with the inner cavity of the bendable tube 5. The distal end of the bendable tube 5 is formed in a taper shape the diameter of which becomes gradually smaller toward the tip of the bendable tube 5.

In order to make the bendable tube 5 more flexible than the multi-lumen tube 2, for example, the bendable tube 5 may be formed from a material more flexible than the multi-lumen tube 2, or the thickness of the bendable tube 5 may be made smaller than the thickness of the multi-lumen tube 2. The bendable tube 5 is retractable in the direction of the central axis (central axis that is coaxial with the central axis O of the multi-lumen tube 2) of the bendable tube 5. When the bendable tube 5 is bent, the inside (inside of the bending) thereof contracts and the outside (outside of the bending) thereof elongates. In the present embodiment, the bendable tube 5 has light permeability. This enables a medical treatment tool, a medical guide wire, or the like delivered toward the distal end of the bendable catheter through the first lumen 2c to be visually recognized from the outside of the bendable tube 5.

As the material of the bendable tube 5, a material having biocompatibility can be employed appropriately. For example, resin materials, such as rubber, silicone, thermoplastic elastomer, or fluororesin, can be used as the material of the bendable tube 5.

The bendable tube 5 is a member that bends by performing bending manipulation on the bendable part 3 using the manipulating part 4 shown in FIG. 1. For this reason, the length of the bendable tube 5 is set as a suitable length according to the nature of treatment using the bendable catheter 1. For example, when performing the treatment of inserting the bendable part 3 of the bendable catheter 1 into the bile duct from the duodenal papilla, the length of the bendable tube 5 is set to a length such that the bendable tube 5 can be bent within a lumen from the duodenal papilla to the bile duct. Specifically, in the case where the bendable tube 5 is bent within a common duct between the duodenal papilla and the bile duct, it is preferable that the length of the bendable tube 5 in the direction of the central axis be less than or equal to 12 mm If the length of the bendable tube 5 in the direction of the central axis is less than or equal to 12 mm, in the case of a normal human body, the bendable tube 5 can be bent by 90° or more without damaging the inner wall surface of the common duct. In addition, the distal end of the bendable tube 5 can be made more flexible than the proximal end thereof, or the proximal end of the bendable tube 5 can also be made more flexible than the distal end. In these cases, a portion with relatively high flexibility in the bendable tube 5 is bent more easily, so that the shape of the bendable part 3 when the bendable part 3 is bent can be a shape suitable for the nature of treatment.

Figure 4:
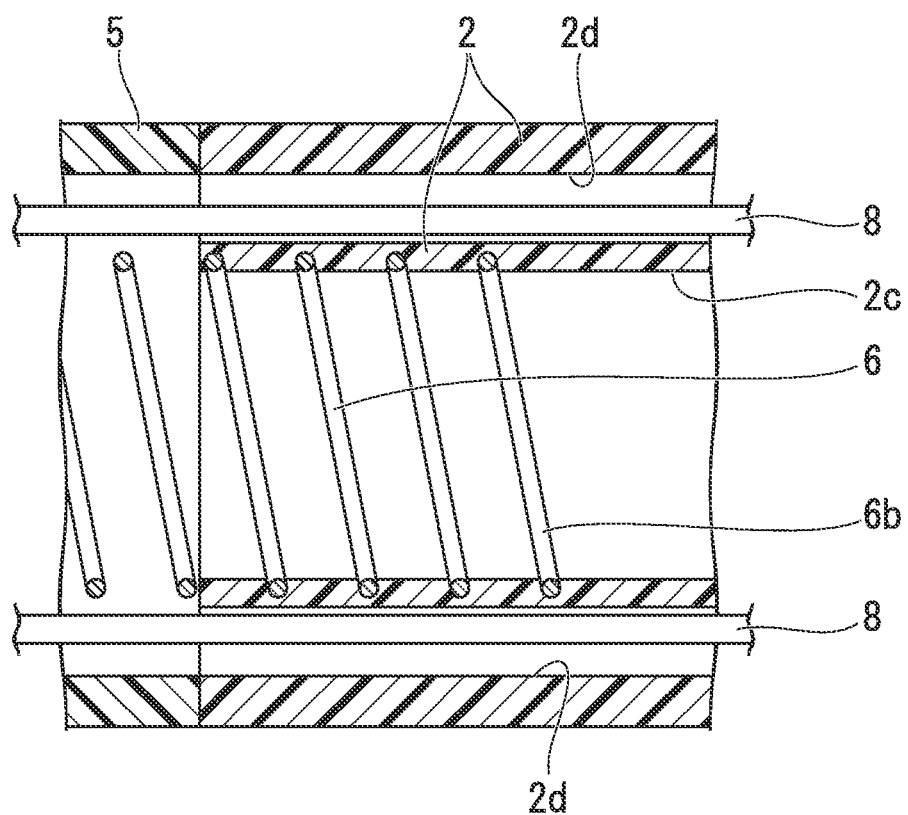
FIG. 4 is a cross-sectional view showing a portion of FIG. 3 to be enlarged.

FIG. 4 is a cross-sectional view showing a portion indicated by symbol X1 in FIG. 3 to be enlarged. As shown in FIGS. 3 and 4, the first coil 6 is a cylindrical coil in which a distal end 6a is arranged in the internal space of the bendable tube 5, and is formed by winding a metal wire rod spirally. The first coil 6 is a loosely wound coil in which adjacent metal wire rods are not in close contact with each other. That is, the winding interval of the first coil 6 is larger than the diameter of the metal wire rod of the first coil 6. In an unloaded condition where an external force is not applied to the first coil 6, a gap is present between the adjacent metal wire rods of the first coil 6. The external diameter of the first coil 6 is slightly larger than the internal diameter of the first lumen 2c of the multi-lumen tube 2, and the internal diameter of the first coil 6 is approximately equal to the internal diameter of the first lumen 2c. A proximal end 6b of the first coil 6 is inserted into the first lumen 2c of the multi-lumen tube 2, and is fixed to the inner peripheral surface of the first lumen 2c by heat welding. This connects the proximal end of the first coil 6 to the first lumen 2c. The internal space of the first coil 6 communicates with the inside of the first lumen 2c, so that the above-described medical treatment tool or guide wire can be inserted therethrough so as to be able to advance and retract.

Figure 5A:
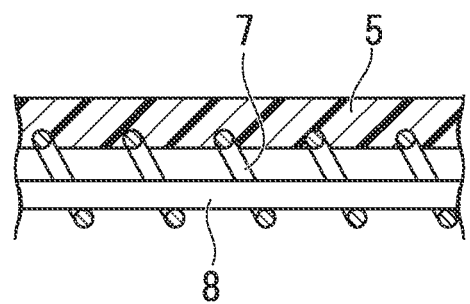
FIG. 5A is a cross-sectional view showing another portion of FIG. 3 to be enlarged.
Figure 5B:
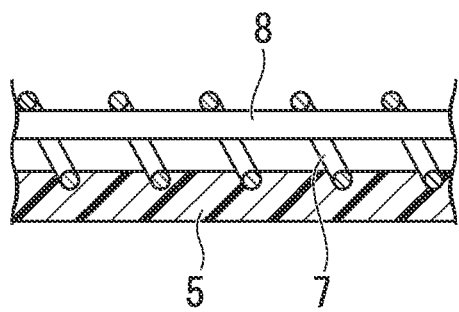
FIG. 5B is a cross-sectional view showing still another portion of FIG. 3 to be enlarged.

FIGS. 5A and 5B are cross-sectional views showing a portion of FIG. 3 to be enlarged, FIG. 5A shows a portion indicated by symbol X2 in FIG. 3, and FIG. 5B shows a portion indicated by symbol X3 in FIG. 3. As shown in FIGS. 3, 5A and 5B, the second coil 7 is a cylindrical coil provided at each of two locations that sandwich the first coil 6 therebetween inside the bendable tube 5, and is formed by winding a metal wire rod spirally. As shown in FIG. 3, each second coil 7 is provided adjacent to the first coil 6, and the central axis of each second coil 7 extends parallel to the central axis of the first coil 6.

Figure 6:
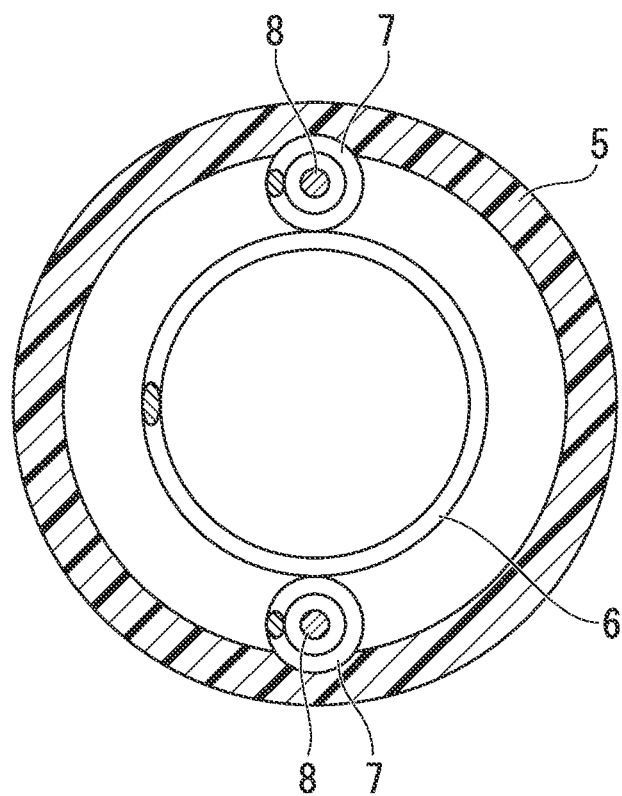
FIG. 6 is a cross-sectional view in a line C-C of FIG. 3.

FIG. 6 is a cross-sectional view in a line C-C of FIG. 3. As shown in FIG. 6, as seen from the direction of the central axis of each second coil 7, the outer peripheral portion of each second coil 7 and the outer peripheral portion of the first coil 6 come into contact with each other. As shown in FIGS. 5A, 5B, and 6, a portion of the outer peripheral portion of each second coil 7 is fixed to the inner surface of the bendable tube 5 by heat welding. Thereby, a portion of the metal wire rod of each second coil 7 is buried in the bendable tube 5 to such a depth that the inner peripheral surface of the bendable tube 5 does not protrude inward more than the inner peripheral portion of each second coil 7. The other portion of the metal wire rod of each second coil 7 is provided so as to be exposed to the internal space of the bendable tube 5. The internal diameter of each second coil 7 is set to be larger than the diameter of the bending manipulation wire 8 to be described below so that the bending manipulation wire 8 can be inserted through the second coil 7 so as to be able to advance and retract.

As shown in FIG. 3, a distal end 7a of each second coil 7 is arranged adjacent to the distal end 6a of the first coil 6. A proximal end 7b of each second coil 7 is located ahead of (closer to the distal end of the bendable catheter 1) the opening at the distal end of the first lumen 2c and the opening at the distal end of each second lumen 2d. That is, the first coil 6 is longer than the second coils 7, and a heat-welded portion between the first coil 6 and the multi-lumen tube 2 is provided closer to the proximal end of the bendable catheter 1 than the second coils 7.

Since both the first coil 6 and the second coils 7 are formed of a metal wire rod, these coils appear on an X-ray transparent image. This allows the bending state of the bendable part 3 to be confirmed by the X-ray transparent image, for example, when the bendable part 3 is inserted into the inside of the body.

The bending manipulation wire 8 is a flexible wire rod that has a distal end 8a and a proximal end 8b. Two bending manipulation wires 8 are provided, and the distal end 8a of each bending manipulation wire 8 is fixed to the metal wire rod of the distal end 7a of each second coil 7 (or to the metal wire rod of each second coil 7 near the distal end 7a). As a method of fixing the distal end 8a of each bending manipulation wire 8 and the distal end 7a of each second coil 7, brazing, soldering, welding or the like can be employed.

As shown in FIG. 1, the proximal end 8b of each bending manipulation wire 8 is fixed to a handle portion 10 (to be described below) in the manipulating part 4.

Each bending manipulation wire 8 has a strength such that the bending manipulation wire 8 does not break even if the bendable part 3 is bent to the maximum in the bendable range thereof when the bending manipulation wire 8 is further pulled toward a manipulator's hand from the proximal end 2b of the multi-lumen tube 2. As materials for such bending manipulation wires 8, metallic materials such stainless steel and titanium or alloy materials thereof, textile materials containing carbon fibers, or the like can be employed.

The manipulating part 4 is arranged near the hands of the manipulator who manipulates the bendable catheter 1. The manipulating part 4 includes a body portion 9 and a port portion 13.

The body portion 9 is a substantially rod-shaped member having a distal end 9a fixed to the proximal end 2b of the multi-lumen tube 2, and has the handle portion 10 and a proximal end ring 12.

The handle portion 10 has a first handle 10a and a second handle 10b that are provided so as to be linearly movable (movable in the axial direction of the body portion 9) with respect to the body portion 9. The first handle 10a and the second handle 10b are arranged to face each other with the body portion 9 interposed therebetween, and able to linearly move individually with respect to the body portion 9. The proximal ends 8b of the bending manipulation wires 8 are fixed to the first handle 10a and the second handle 10b, respectively. Each of the first handle 10a and the second handle 10b is formed with a finger-hooking portion 11 to which a manipulator's fingers are hooked. The finger-hooking portion 11 is formed so as to protrude outward in the radial direction of the body portion 9. The manipulator can pull the bending manipulation wires 8 fixed to the first handle 10a and the second handle 10b toward the proximal end of the bendable catheter 1 by hooking his/her fingers to the finger-hooking portion 11 and pulling the finger-hooking portion 11 toward the proximal end.

The proximal end ring 12 is provided at the proximal end 9b of the body portion 9, and is formed in a cylindrical shape or an annular shape that has the central axis extending in a direction orthogonal to the longitudinal axis of the body portion 9. The cylindrical or annular portion of the proximal end ring 12 is formed with an internal diameter such that a user can insert his/her finger therethrough.

The port portion 13 has an opening portion 13a that communicates with the first lumen 2c (refer to FIG. 3) and opens to the outside. The port portion 13 is an instrument to insert a medical treatment tool, a medical guide wire, or the like into the first lumen 2c through the opening portion 13a. Additionally, an air and water supply pump or a suction pump can also be connected to the opening portion 13a of the port portion 13, and air supply, water supply, or suction can be performed through the port portion 13.

Additionally, in the present embodiment, in addition to the opening portion 13a, a second opening portion 13b formed to communicate with the first lumen 2c is provided in the port portion 13 in order to inject a medical solution or a contrast medium. This enables the medical solution or the contrast medium to be discharged from the distal end of the bendable part 3 through the gap of the first lumen 2c, with the medical treatment tool or the medical guide wire being attached to the bendable catheter 1 through the opening portion 13a.

The working and effects of the bendable catheter 1 with the configuration described above will be described using an example in which a human body is treated using the bendable catheter 1.

Usage Example 1

Figure 7:
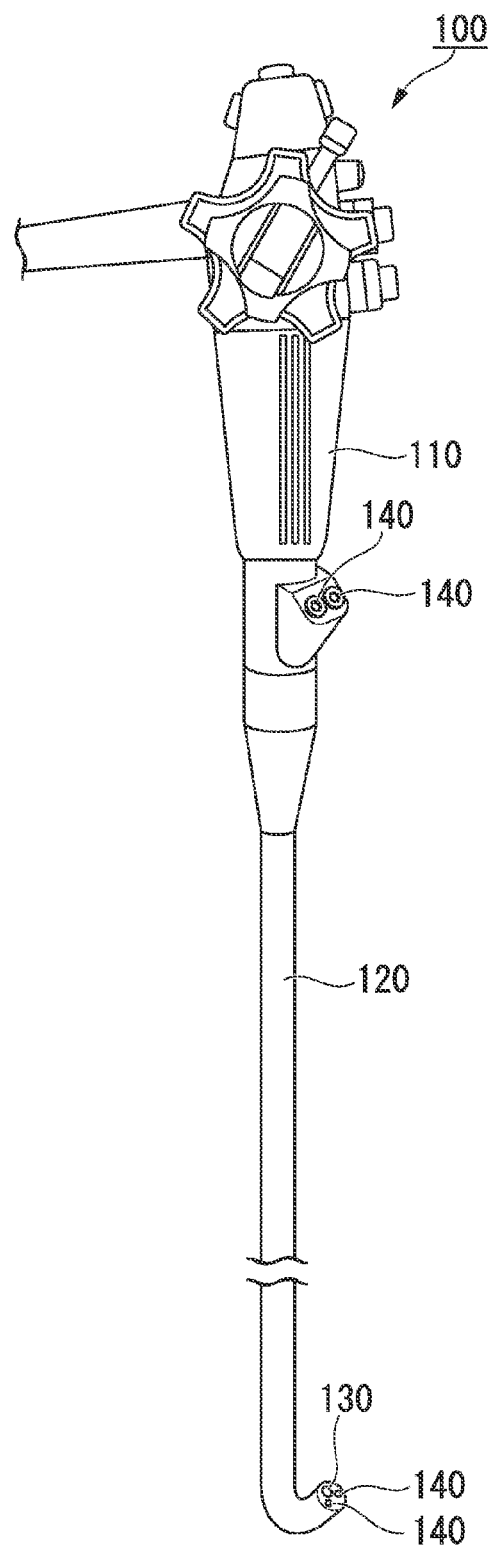
FIG. 7 is a view showing an example of an endoscope apparatus in the embodiment of the present invention.
Figure 8A:
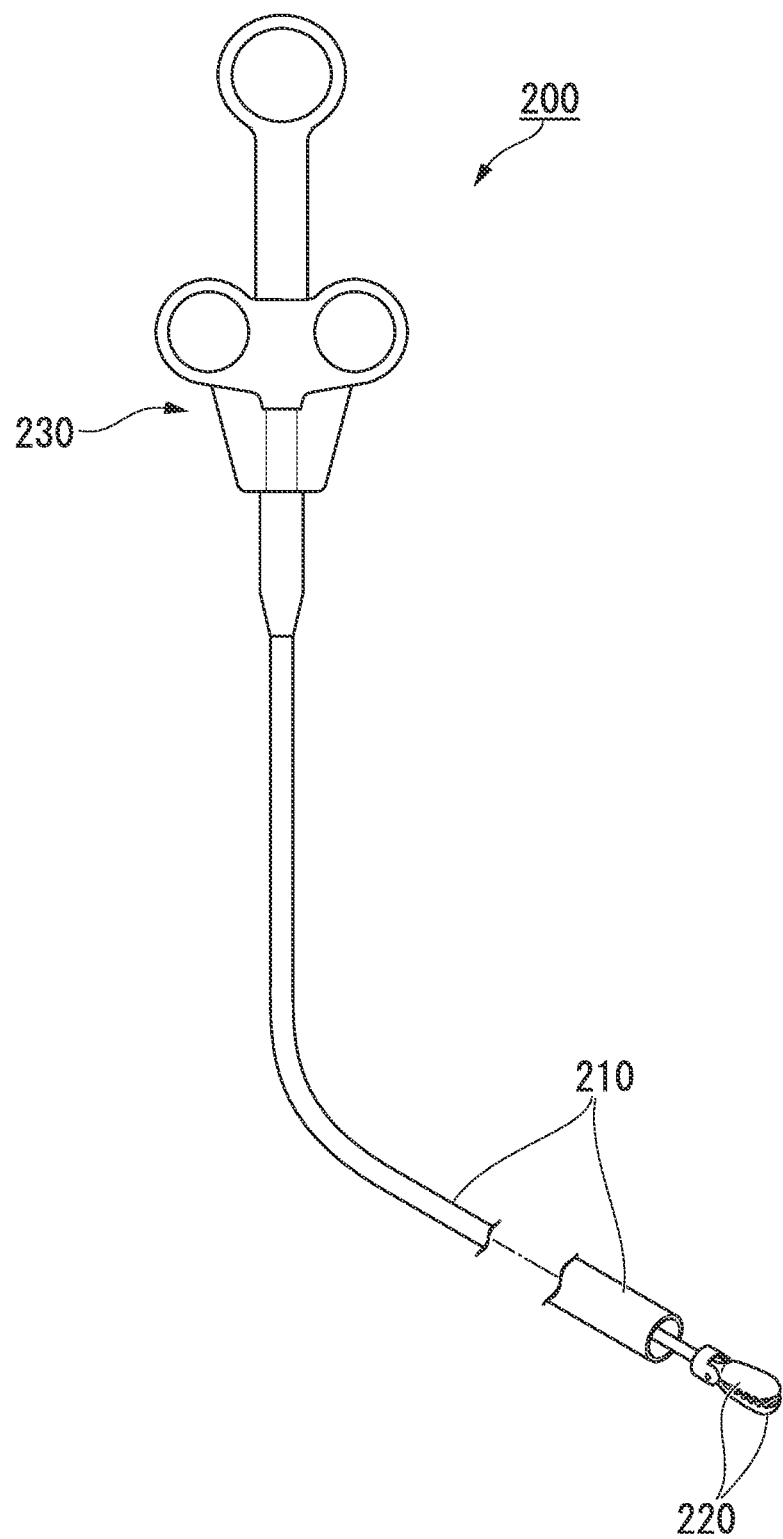
FIG. 8A is a view showing an example of a first treatment tool in the embodiment of the present invention.
Figure 8B:
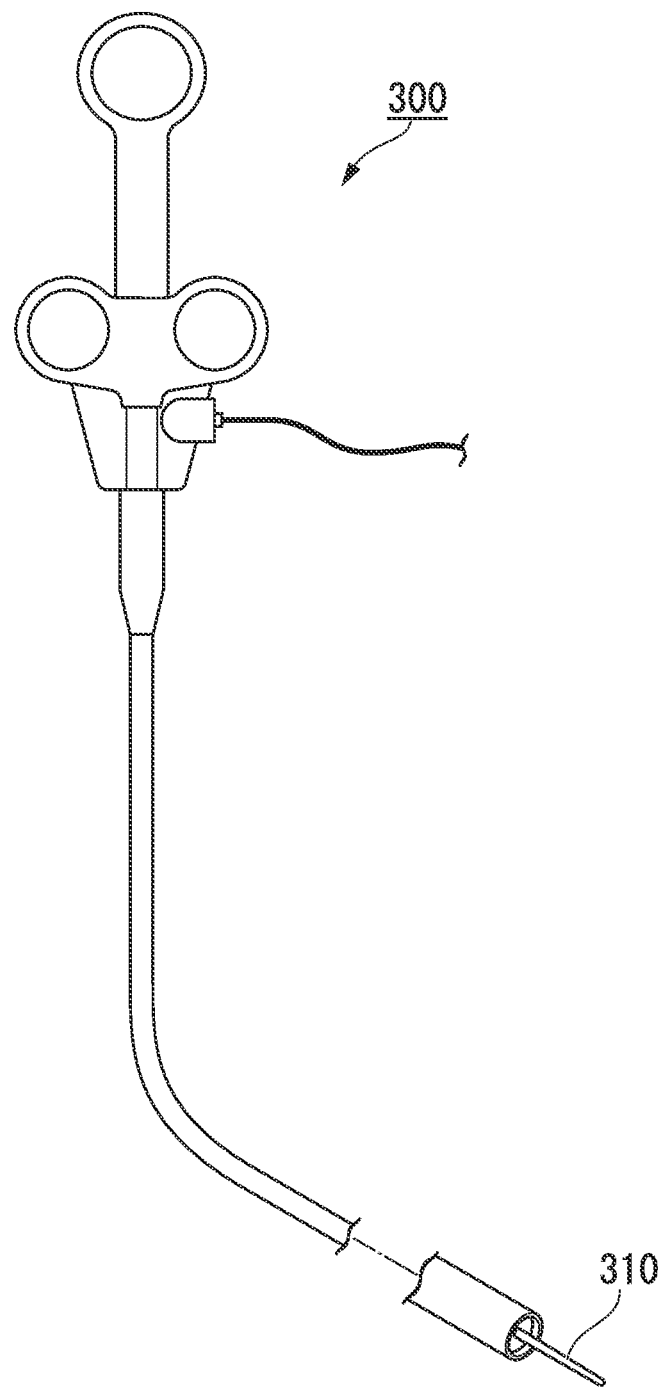
FIG. 8B is a view showing an example of a second treatment tool in the embodiment of the present invention.

FIG. 7 is a view showing an example of an endoscope apparatus 100 to be used for treatment along with the bendable catheter 1. FIG. 8A is a view showing an example of a first treatment tool 200 to be used for treatment along with the bendable catheter 1, and FIG. 8B is a view showing an example of a second treatment tool 300 to be used for treatment along with the bendable catheter 1.

An example will be described in which treatment is performed on a lesion caused within a lumen tissue of a human body by combining the bendable catheter 1 of the present embodiment, the endoscope apparatus 100 (refer to FIG. 7) including an imaging part 130, and a medical treatment tool (the first treatment tool 200, refer to FIG. 8A) inserted through the bendable catheter 1. The working and effects of the bendable catheter 1 will be described using this example.

As shown in FIG. 7, the endoscope apparatus 100 to be used in the present usage example has an endoscope body 110, an insertion part 120 provided to extend from the endoscope body 110, and an imaging part 130 that is provided at the distal end of the insertion part 120 to capture a front image in the insertion direction. The insertion part 120 is provided with a plurality of treatment tool channels 140 through which the bendable catheter 1 or other treatment tools are inserted, and the bendable catheter 1 or other treatment tools can be delivered from the distal end of the insertion part 120. The endoscope apparatus 100 that can be used in the present usage example may be configured such that the internal diameter of at least one of the plurality of treatment tool channels 140 is larger than the maximum external diameter of the bendable part 3 and the multi-lumen tube 2 of the bendable catheter 1.

As shown in FIG. 8A, the first treatment tool 200 used while being inserted into the bendable catheter 1 in the present usage example includes an insertion part 210 having an external diameter capable of being inserted through the inside of the port portion 13 (refer to FIG. 1) and the insides of the first lumen 2*c* and the first coil 6 (refer to FIG. 3) so as to be able to advance and retract, a pair of forceps 220 provided at the distal end of the insertion part 210 capable of being opened and closed, and a manipulating part 230 provided at the proximal end of the insertion part 210 and to open and close the pair of forceps.

Additionally, in the present usage example, in addition to the first treatment tool 200, an endoscopic high-frequency incision tool (a second treatment tool 300, refer to FIG. 8B) having a needlelike electrode 310 to incision a body tissue is used in combination with the endoscope apparatus 100.

Figure 9:
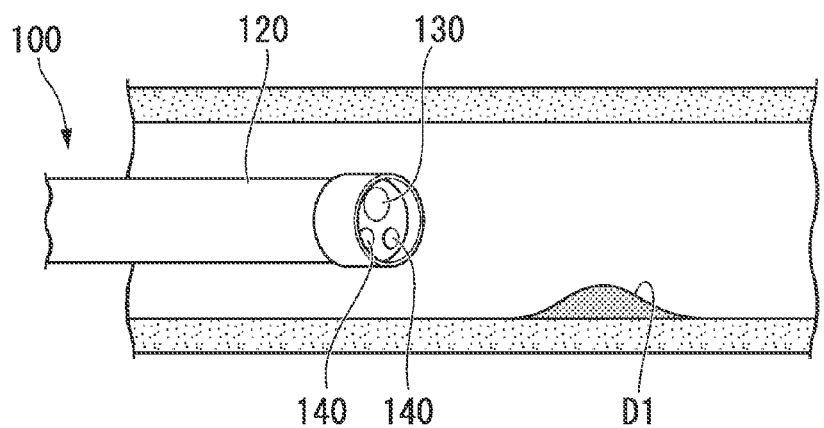
FIG. 9 is a schematic view showing one process of treatment using the bendable catheter in the embodiment of the present invention.

A procedure using the endoscope apparatus 100, the first treatment tool 200, the second treatment tool 300, and the bendable catheter 1 of the present embodiment will be described next. FIG. 9 is a schematic view showing one process of treatment using the bendable catheter 1.

In the present usage example, the insertion part 120 of the endoscope apparatus 100 is inserted into the inside of the body from natural openings, such as a patient's mouth and anus, and as shown in FIG. 9, the distal end of the insertion part 120 is guided to a lesion D1 that requires treatment.

If the distal end of the insertion part 120 has reached the lesion D1, the lesion D1 is observed using the imaging part 130 provided at the distal end of the insertion part 120, and the lesion D1 is diagnosed.

Figure 10A:
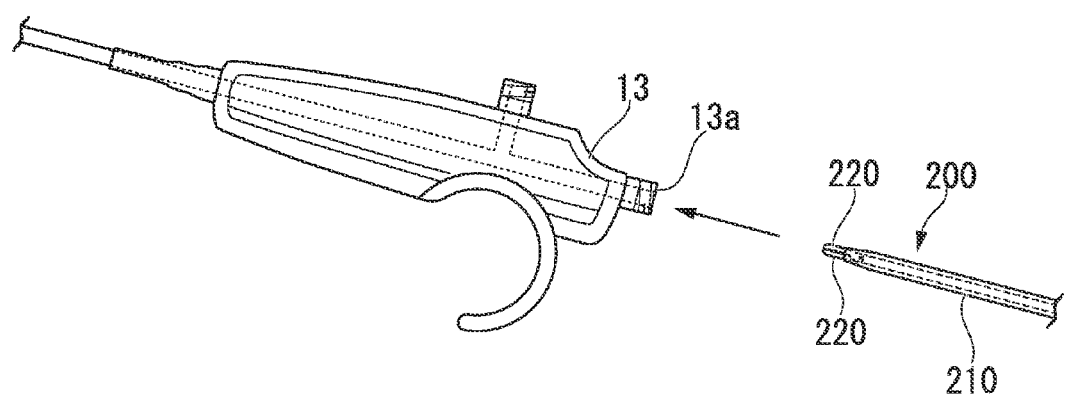
FIG. 10A is a schematic view showing an example in which the first treatment tool is attached to the bendable catheter in the embodiment of the present invention.
Figure 10B:
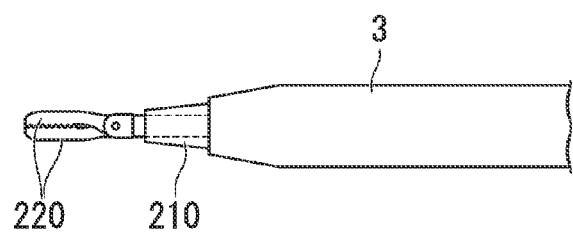
FIG. 10B is a schematic view showing another example in which the first treatment tool is attached to the bendable catheter in the embodiment of the present invention.

FIGS. 10A and 10B are schematic views showing an example in which the first treatment tool 200 is attached to the bendable catheter 1. In a case where the lesion D1 requires treatment as a result of diagnosing the lesion D1, as shown in FIGS. 10A and 10B, the first treatment tool 200 is inserted into the port portion 13 of the bendable catheter 1, and the first treatment tool 200 is attached to the bendable catheter 1 so that the pair of forceps 220 is arranged in the state of protruding from the distal end of the bendable part 3.

Figure 11:
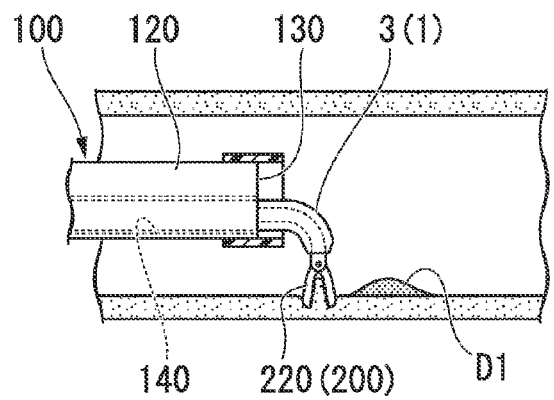
FIG. 11 is a schematic view showing one process of treatment using the bendable catheter in the embodiment of the present invention.
Figure 12A:
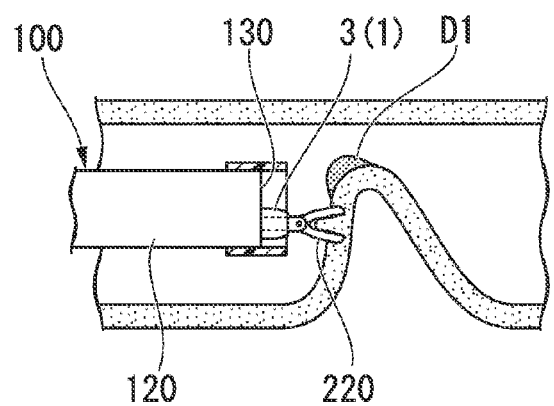
FIG. 12A is a schematic view showing one process of treatment using the bendable catheter in the embodiment of the present invention.
Figure 12B:
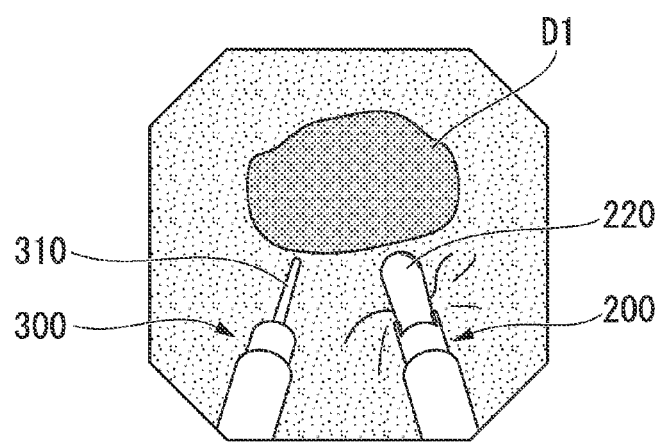
FIG. 12B is a schematic view showing an endoscopic image when treatment is performed using the bendable catheter in the embodiment of the present invention.

FIGS. 11 and 12A are schematic views showing one process of treatment using the bendable catheter 1. FIG. 12B is a schematic view showing an endoscopic image when treatment is performed using the bendable catheter 1.

As shown in FIG. 11, a manipulator inserts the bendable catheter 1 to which the first treatment tool 200 is attached, into the inside of the treatment tool channel 140 of the endoscope apparatus 100, and makes the distal end portion of the bendable catheter 1 protrude from the distal end of the insertion part 120 of the endoscope apparatus 100.

Next, as indicated by an arrow in FIG. 1, the first handle 10*a* or the second handle 10*b* of the manipulating part 4 of the bendable catheter 1 is pulled toward the proximal end of the bendable catheter 1. For example, if the first handle 10*a* is pulled toward the proximal end, the bending manipulation wire 8 fixed to the first handle 10*a* moves toward the proximal end, and one second coil 7 (refer to FIG. 3) fixed to the distal end of the bending manipulation wire 8 is compressed in the direction of the central axis. Since the metal wire rod of the second coil 7 is fixed to the inner surface of the bendable tube 5, if the second coil 7 contracts, the portion of the bendable tube 5 fixed to the second coil 7 contracts in the direction of the central axis. In addition, compressive force in the direction of the central axis is also applied to the multi-lumen tube 2 by the pulling of the bending manipulation wire 8. However, since the bendable tube 5 is more flexible than the multi-lumen tube 2, only the portion of the bendable tube 5 fixed to the second coil 7 can be contracted with the shape of the multi-lumen tube 2 being held. Thereby, as shown in FIG. 1, the bendable tube 5 bends toward the contracting second coil 7 of the two second coils 7.

If the bendable tube 5 bends, the first coil 6 arranged within the bendable tube 5 also bends along with the bendable tube 5. The first coil 6 supports the inner surface of the bendable tube 5 so that the shape of the bendable tube 5 as seen in a section orthogonal to the central axis of the bendable tube 5 is kept circular.

Thereby, even if the bendable part 3 is bent, the bendable tube 5 is not crushed, and the inner cavity of the bendable tube 5 can be prevented from being plugged. Even in a state where the bendable tube 5 is bent, an insertion part (for example, the insertion part 210 of the first treatment tool 200) of a medical treatment tool can be advanced and retracted and rotated. Additionally, since the inner cavity of the bendable tube 5 can be prevented from being plugged, the bendable part 3 can be bent largely compared to the related-art catheter.

As shown in FIG. 11, if the bendable part 3 of the bendable catheter 1 to which the first treatment tool 200 is attached is bent, the pair of forceps 220 of the first treatment tool 200 can be directed to an inner wall of a lumen tissue, with the insertion part 120 of the endoscope apparatus 100 being directed to the direction of the central axis of the lumen tissue. That is, the pair of forceps 220 can be directed to a direction orthogonal to the direction of the central axis of the lumen tissue, and the pair of forceps 220 can be directed perpendicularly to the inner wall of the lumen tissue.

As shown in FIG. 12A, the manipulator manipulates the manipulating part 230 (refer to FIG. 8A) of the first treatment tool 200, opens and closes the pair of forceps 220, grips a body tissue near the lesion D1, and pulls the body tissue along with the bendable catheter 1 toward the proximal end thereof. Thereby, as shown in FIG. 12B, the lesion D1 can be moved into the visual field of the imaging part 130 of the endoscope apparatus 100. That is, the lesion D1 can be moved to a position where treatment is easily performed on the lesion D1.

Next, the above-described high-frequency incision tool (the second treatment tool 300) is inserted into the treatment tool channel 140 (refer to FIG. 7) of the endoscope apparatus 100, and as shown in FIG. 12B, the lesion D1 is excised using the needlelike electrode 310 of the second treatment tool 300 while observing an endoscopic image. Then, the excised lesion D1 is gripped with the pair of forceps 220, and is taken out to the outside of the body through the treatment tool channel 140.

Previously, in a case where treatment is performed on a lesion caused in the inner wall of a lumen tissue, the insertion part of the endoscope apparatus is bent within the lumen tissue to capture the lesion within the visual field of the imaging part, and a suitable treatment tool for an endoscope apparatus is inserted into the treatment tool channel in this state. Since it is difficult to bend the insertion part of the endoscope apparatus largely, it is difficult to capture the lesion at a suitable position within the visual field of the imaging part in a case where there is no space for bending the insertion part of the endoscope apparatus within the lumen tissue. For this reason, previously, complicated work of advancing and retracting or twisting the insertion part of the endoscope apparatus within the lumen tissue is required.

In contrast, in the present usage example, the insertion part 210 of the first treatment tool 200 can be bent by bending the bendable part 3 of the bendable catheter 1. For this reason, even with the insertion part 120 of the endoscope apparatus 100 being parallel to the longitudinal axis of the lumen tissue, a body tissue near the lesion D1 can be gripped with the pair of forceps 220 of the first treatment tool 200. Additionally, the lesion D1 can be moved to a suitable position within the visual field of the imaging part 130 by pulling the bendable catheter 1 toward the proximal end. As a result, by using the bendable catheter 1, the operation for performing treatment on the lesion D1 can be simplified further, and treatment on the lesion D1 can be made easier than before.

Usage Example 2

Another example will be described in which treatment is performed on a lesion caused within a lumen tissue of a human body by combining the bendable catheter 1 of the present embodiment, the endoscope apparatus 100, and a third medical treatment tool inserted through the bendable catheter 1. The working and effects of the bendable catheter 1 will be described using this example.

In the present usage example, an example in which treatment is performed on a lesion caused inside the tissue of a lumen tissue is illustrated.

In the present usage example, the same endoscope apparatus 100 as the above-described Usage Example 1, and an injection needle for an endoscope that can be used while being inserted into the inside of the bendable catheter 1 that is the third treatment tool are used.

Figure 13A:
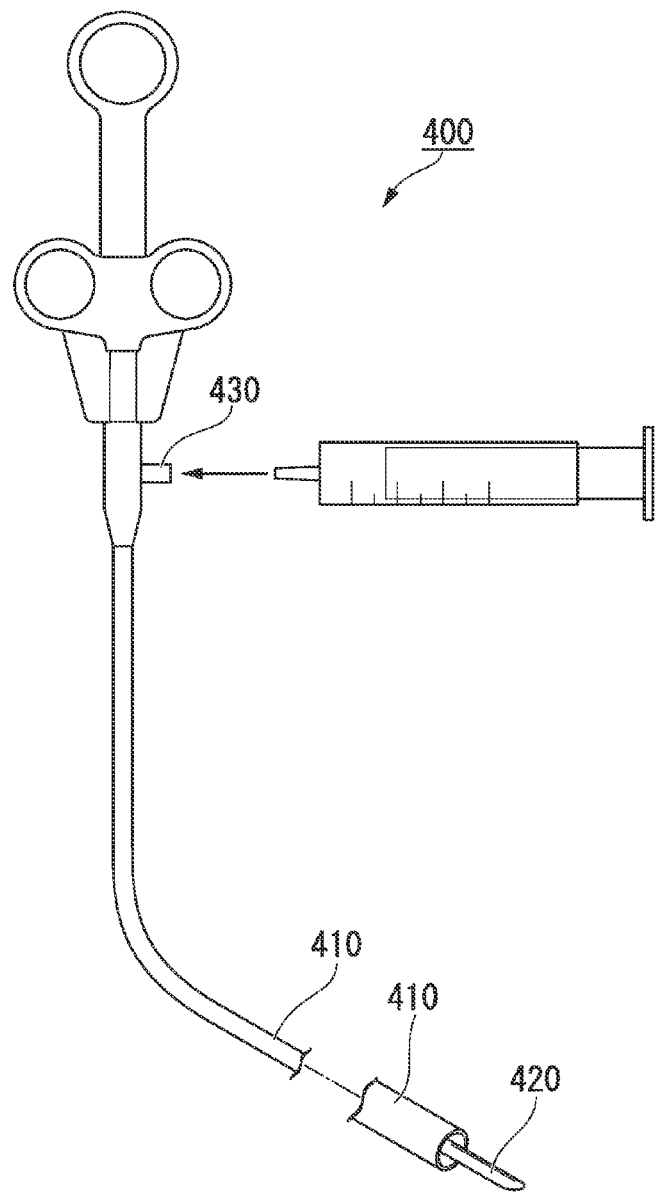
FIG. 13A is a view showing an example of a third treatment tool in the embodiment of the present invention.
Figure 13B:
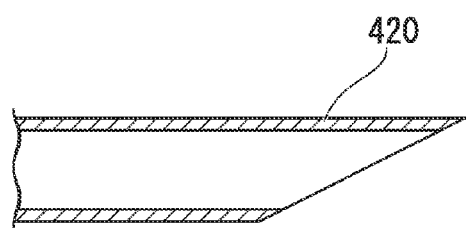
FIG. 13B is a cross-sectional view showing a portion of the third treatment tool shown in FIG. 13A to be enlarged.

FIG. 13A is a view showing an example of a third treatment tool 400 to be used for treatment along with the bendable catheter 1. FIG. 13B is a cross-sectional view showing a portion of the third treatment tool 400 to be enlarged.

As shown in FIGS. 13A and 13B, the third treatment tool 400 (injection needle for an endoscope) includes a tubular insertion part 410 that can be inserted inside the bendable catheter 1 so as to be able to advance and retract, an injection needle 420 provided at the distal end of the insertion part 410 and having an inner cavity communicating with an inner cavity of the insertion part 410, and a medical solution injection port 430 provided at the proximal end of the insertion part 410.

Figure 14:
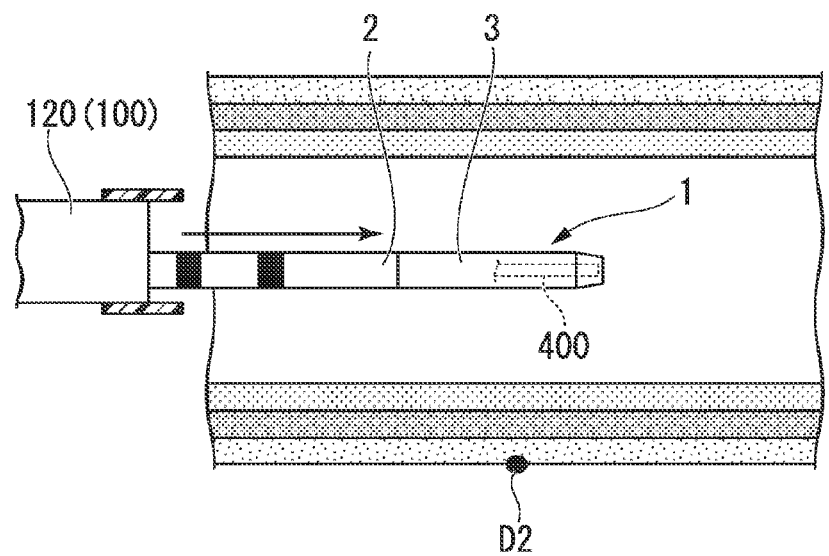
FIG. 14 is a schematic view showing one process of treatment using the bendable catheter in the embodiment of the present invention.
Figure 15:
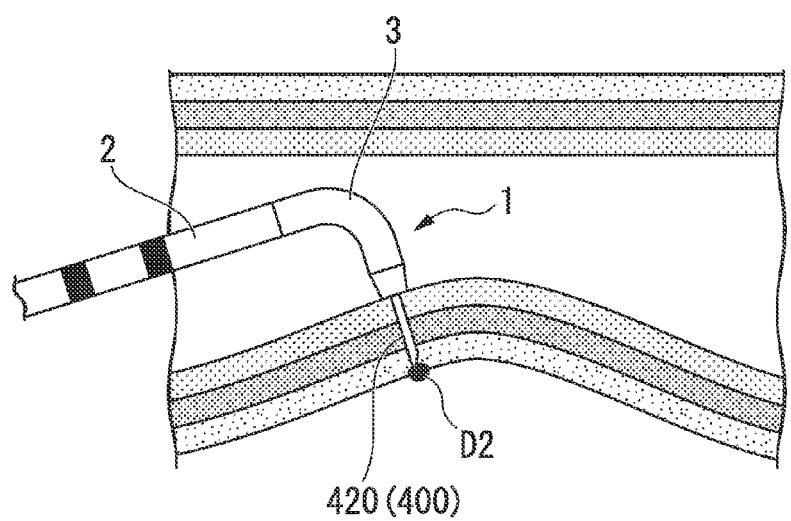
FIG. 15 is a schematic view showing one process of treatment using the bendable catheter in the embodiment of the present invention.

FIGS. 14 and 15 are schematic views showing one process of treatment using the bendable catheter 1.

As shown in FIG. 14, in the case of the present usage example, a lesion D2 is located not at the surface of the inner wall of a lumen tissue but at the external surface of the lumen tissue. In the present usage example, similarly to the above-described Usage Example 1, the insertion part 120 of the endoscope apparatus 100 is inserted into the inside of the body, and the distal end of the insertion part 120 is guided to the vicinity of the lesion D2.

If the distal end of the insertion part 120 is guided to the vicinity of the lesion D2, the third treatment tool 400 is inserted into the inside of the bendable catheter 1, and the third treatment tool 400 is attached to the bendable catheter 1 so that the injection needle 420 can be delivered from the distal end of the bendable part 3. Moreover, the bendable catheter 1 is inserted into the treatment tool channel 140 of the endoscope apparatus 100 along with the third treatment tool 400, and the distal end portion of the bendable catheter 1 is made to protrude from the distal end of the insertion part 120 of the endoscope apparatus 100.

The manipulator pulls the first handle 10a or the second handle 10b of the manipulating part 4 (refer to FIG. 1) of the bendable catheter 1 toward the proximal end thereof, and as shown in FIG. 15, bends the bendable part 3. Then, the orientation of the bendable part 3 is changed to the radial direction of the lumen tissue. In addition, at this time, the injection needle 420 of the third treatment tool 400 is accommodated within the bendable part 3. The manipulator can visually recognize the markings M, the first coil 6, and the second coils 7 using an X-ray image, and can confirm that the bendable part 3 is bent toward the lesion D2. In addition, alignment between the distal end of the bendable part 3 and the lesion D2 may be performed using an ultrasonic endoscope that radiates ultrasonic waves from the inside of the lumen tissue toward the lesion D2 to generate an image of the lesion D2.

The manipulator delivers the injection needle 420 from the bendable part 3 to puncture the lumen tissue with the injection needle 420 in a state where the distal end of the bendable part 3 is directed to the lesion D2, and makes the distal end of the injection needle 420 reach the lesion D2. Moreover, treatment is performed by supplying a medical solution to the distal end of the insertion part 410 from the medical solution injection port 430 (refer to FIG. 13A) of the proximal end of the insertion part 410 and by injecting the medical solution into the lesion D2.

In the present usage example, similarly to the above-described Usage Example 1, even in a case where there is not sufficient space for changing the orientation of the insertion part 120 of the endoscope apparatus 100 within the lumen tissue, the orientation of the injection needle 420 to be used along with the endoscope apparatus 100 can be changed by changing the orientation of the bendable part 3. Thus, treatment can be reliably performed on the lesion D2.

Additionally, since the injection needle 420 can be inserted into the inner wall surface of the lumen tissue at a larger angle (at an angle more closely perpendicular to the inner wall surface), a medical solution can be injected into the lesion D2 at a deeper position using the injection needle 420.

In addition, although the example in which a medical solution is injected using the injection needle is shown in Usage Example 2, treatment can be similarly performed on the lesion D2 by using a needlelike probe that emits radiofrequency waves or the like along with the bendable catheter 1. In this case, the lesion D2 can be thermally coagulated by puncturing the lesion D2 with this probe.

Additionally, instead of injecting the medical solution, the treatment of indwelling a marker formed of a material appearing on an X-ray image in the lesion D2 can also be performed by the same method. This enables the position of, for example, a marker indwelled in the lesion D2 to be specified using an X-ray fluoroscope. By radiating radiation rays, such as X rays, with the marker as a target, the lesion D2 can be irradiated with the radiation rays with high precision, and the lesion D2 can be treated.

Usage Example 3

An example will be described in which a treatment tool for an endoscope that removes foreign matter produced in a lumen tissue is guided by combining the bendable catheter 1 of the present embodiment, an endoscope apparatus including an imaging part, and a guide wire inserted into the bendable catheter 1. The working and effects of the bendable catheter 1 will be described using this example.

Figure 16A:
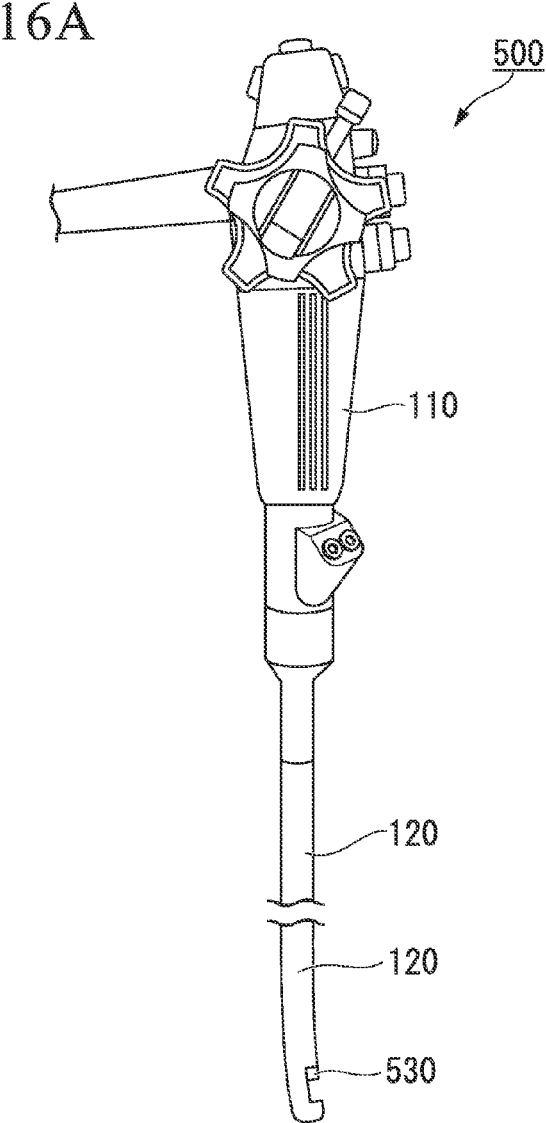
FIG. 16A is a view showing another example of the endoscope apparatus in the embodiment of the present invention.
Figure 16B:
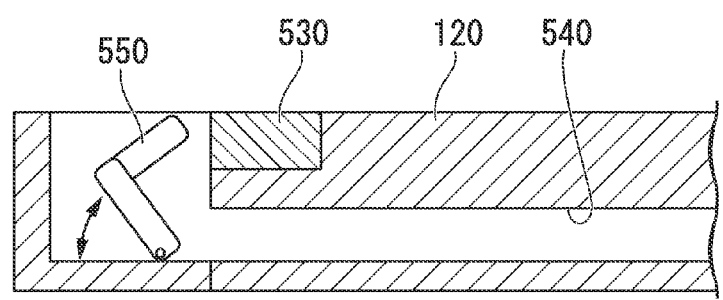
FIG. 16B is a cross-sectional view showing a portion of the endoscope apparatus shown in FIG. 16A to be enlarged.

An example of the bile duct insertion procedure in which the bendable catheter 1 is selectively inserted into the bile duct and treatment to be carried out subsequently is shown in the present usage example. FIG. 16A is a view showing an endoscope apparatus 500 of the present usage example to be used for treatment along with the bendable catheter 1. FIG. 16B is a cross-sectional view showing a distal end portion of the endoscope apparatus 500 shown in FIG. 16A to be enlarged.

As shown in FIGS. 16A and 16B, the endoscope apparatus 500 to be used in the present usage example includes the endoscope body 110, the insertion part 120, and an imaging part 530 provided at the distal end of the insertion part 120. The endoscope apparatus 500 is of a lateral view type different from the endoscope apparatus 100 described in each usage example described above. The distal end of the insertion part 120 of the endoscope apparatus 500 is provided with a raising stand 550 to make the distal end of the bendable catheter 1 or other treatment tools protrude laterally. Even in the endoscope apparatus 500 to be used for the present usage example, similarly to the above-described endoscope apparatus 100, the insertion part 120 is also provided with a treatment tool channel 540 through which a treatment tool or the like is inserted. In addition, in the case of treatment to be described in the present usage example, there should be at least one treatment tool channel 540.

Next, a procedure using the endoscope apparatus 500, the guide wire, a treatment tool for an endoscope, and the bendable catheter 1 of the present embodiment will be described.

Figure 17:
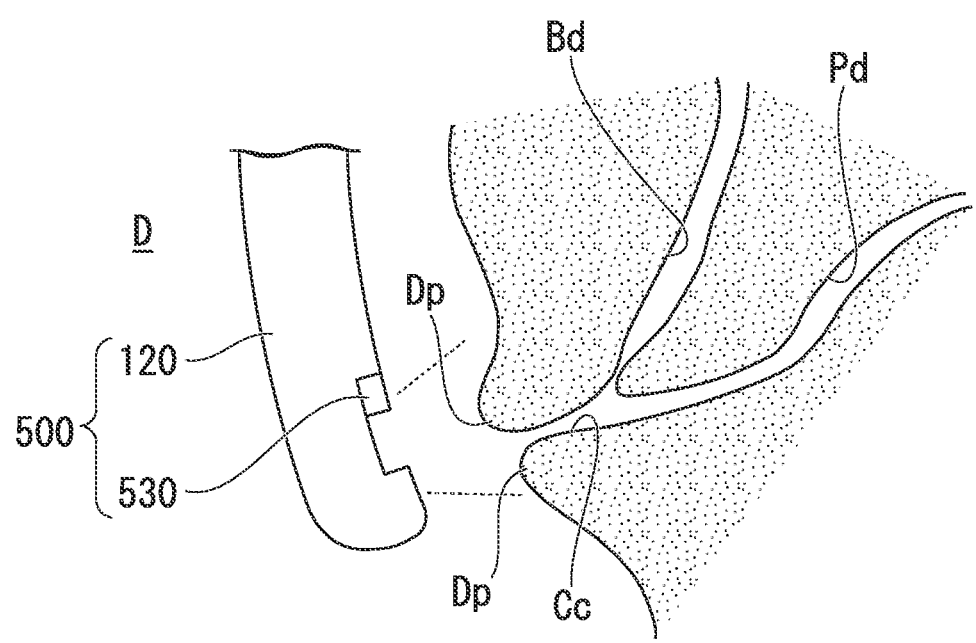
FIG. 17 is a schematic view showing one process of treatment using the bendable catheter and the endoscope apparatus in the embodiment of the present invention.

FIG. 17 is a schematic view showing one process of treatment using the endoscope apparatus 500 and the bendable catheter 1. The manipulator inserts the endoscope apparatus 500 into the inside of the body from a patient's natural opening, and as shown in FIG. 17, guides the distal end of the insertion part 120 of the endoscope apparatus 500 to the duodenal papilla Dp. Moreover, the manipulator captures the duodenal papilla Dp within the visual field of the imaging part 530 of the endoscope apparatus 500.

Figure 18A:
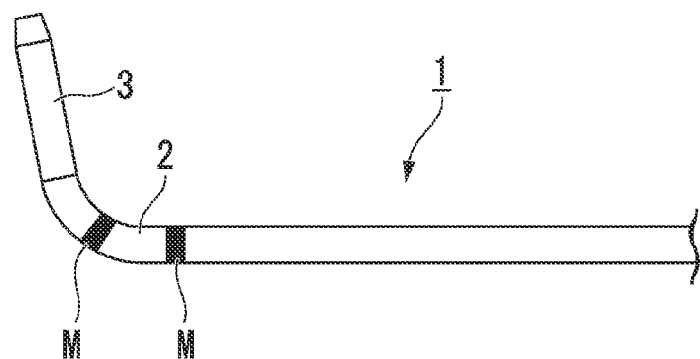
FIG. 18A is a schematic view showing a distal end portion of the bendable catheter in the embodiment of the present invention.
Figure 18B:
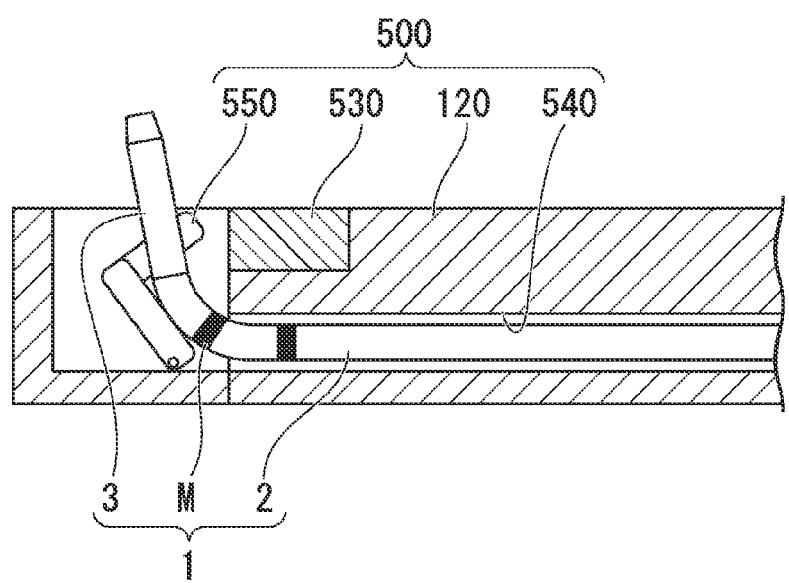
FIG. 18B is a view showing a state where the bendable catheter is attached to the endoscope apparatus in the embodiment of the present invention.

FIG. 18A is a schematic view showing the distal end portion of the bendable catheter 1 when treatment is performed, and FIG. 18B is a view showing a state where the bendable catheter 1 is attached to the endoscope apparatus 500.

As shown in FIGS. 18A and 18B, the manipulator inserts the bendable catheter 1 through the treatment tool channel 540 of the endoscope apparatus 500, and delivers the bendable catheter 1 from the distal end side thereof toward the raising stand 550. If needed, the bendable catheter 1 can be inserted into the treatment tool channel 540 after a bending tendency is given to a portion of the distal end 2a of the multi-lumen tube 2. In a case where the bending tendency is given to the multi-lumen tube 2, the multi-lumen tube 2 runs along the raising stand 550. Thus, positioning of the bendable catheter 1 in the rotational direction (the direction around the central axis of the bendable catheter 1) with respect to the endoscope apparatus 500 becomes easy. In the present usage example, in the procedure of endoscopic approach to the duodenal papilla Dp as shown in FIG. 17, the position of the endoscope apparatus 500 within the duodenum D is determined by a predetermined procedure. For this reason, since the relative position between the bile duct Bd and the endoscope apparatus 500 is approximately determined in a predetermined positional relationship, the bending direction of the bendable part 3 can be easily aligned with the orientation suitable for the procedure of bile duct insertion by giving the bending tendency to the multi-lumen tube 2 in advance.

Figure 19:
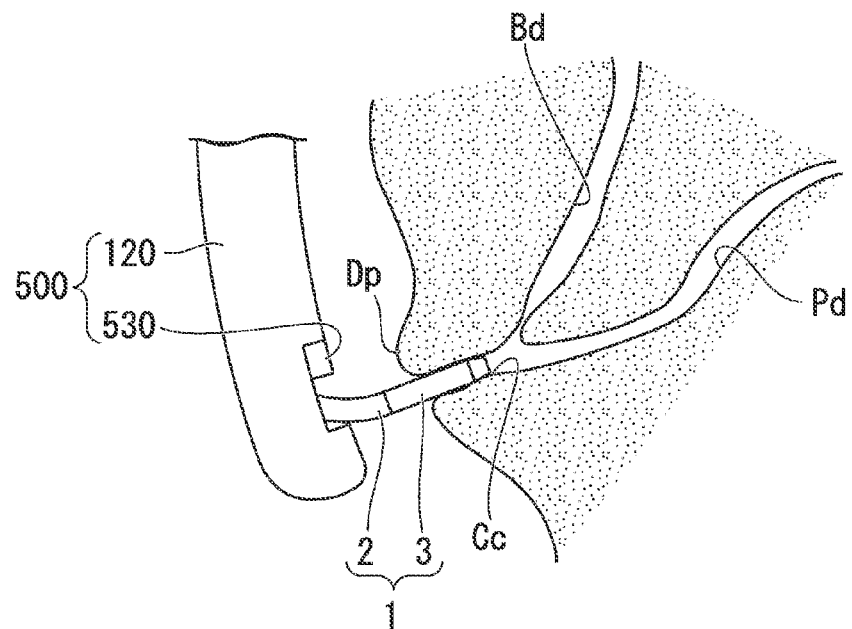
FIG. 19 is a schematic view showing one process of treatment using the bendable catheter in the embodiment of the present invention.
Figure 20:
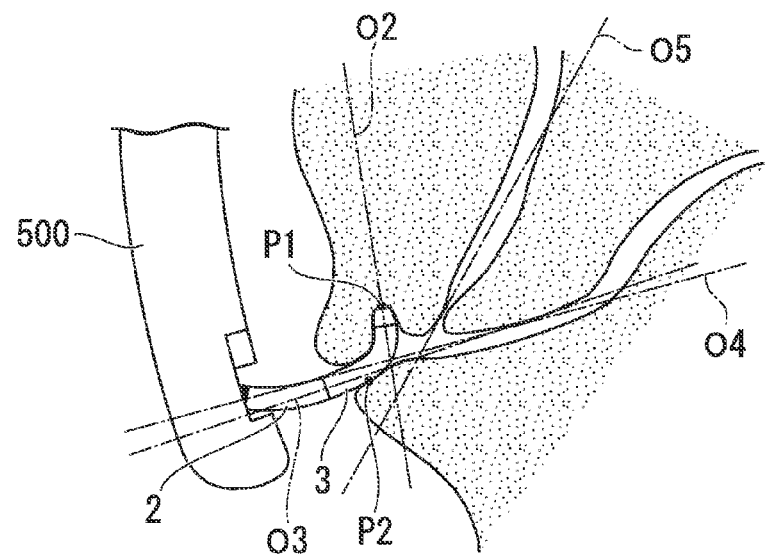
FIG. 20 is a schematic view showing one process of treatment using the bendable catheter in the embodiment of the present invention.

FIGS. 19 and 20 are schematic views showing one process of treatment using the bendable catheter 1. As shown in FIG. 19, the bendable part 3 of the distal end of the bendable catheter 1 is made to protrude from the insertion part 120 of the endoscope apparatus 500, and the bendable part 3 is inserted into a common duct Cc as a lumen tissue from the opening of the duodenal papilla Dp.

Subsequently, the manipulator pulls the first handle 10a or the second handle 10b (refer to FIG. 1) toward the proximal end of the bendable catheter 1. Then, as one bending manipulation wire 8 moves toward the proximal end, the bendable part 3 bends. Then, as shown in FIG. 20, the distal end of the bendable part 3 comes into contact with the duct wall of the common duct Cc substantially perpendicularly. The bendable part 3 bends along a plane where both a central axis O2 of the distal end of the bendable part 3 and a central axis O3 of the proximal end of the bendable part 3 are included (that is, a plane where the pair of bending manipulation wires 8 in the bendable part 3 are included). The direction of the bending operation of the bendable part 3 coincides with a plane where both a central axis O4 of the common duct Cc and a central axis O5 of the bile duct Bd are included.

Additionally, at this time, the bendable part 3 is in contact with two positions (for example, positions indicated by symbol P1 and symbol P2 in FIG. 20) that face the inner wall surface of the common duct Cc approximately perpendicularly, in the plane where both the central axis O2 and O3 are included. Although the bendable part 3 is supported by the inner wall of the common duct Cc and the deviation when the multi-lumen tube 2 is pushed into the common duct Cc is suppressed, there is little damage to the duct wall of the common duct Cc because the inner wall surface of the common duct Cc is dented along the bendable part 3.

Figure 21A:
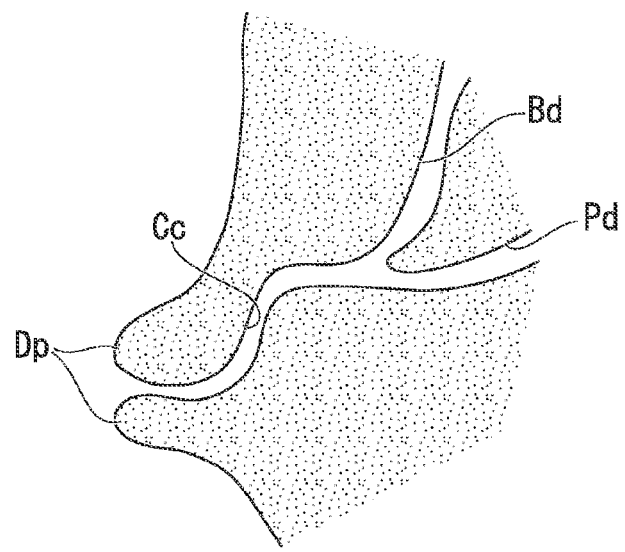
FIG. 21A is a schematic view showing one process in which a distal end of the bendable catheter in the embodiment of the present invention is inserted into the inside of a lumen tissue.
Figure 21B:
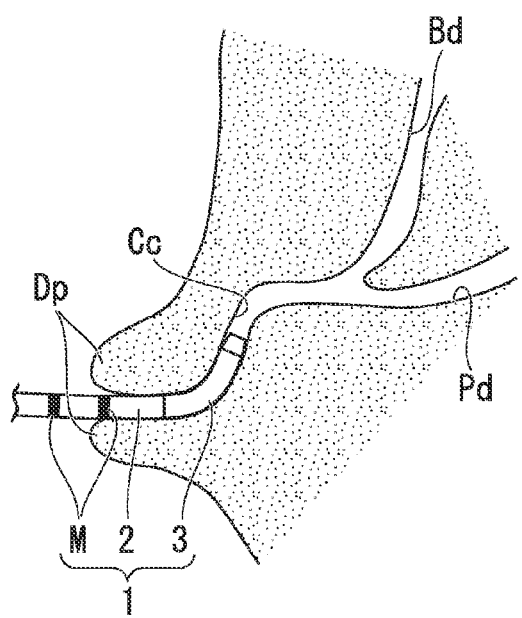
FIG. 21B is a schematic view showing one process in which the distal end of the bendable catheter in the embodiment of the present invention is inserted into the inside of a lumen tissue.
Figure 21C:
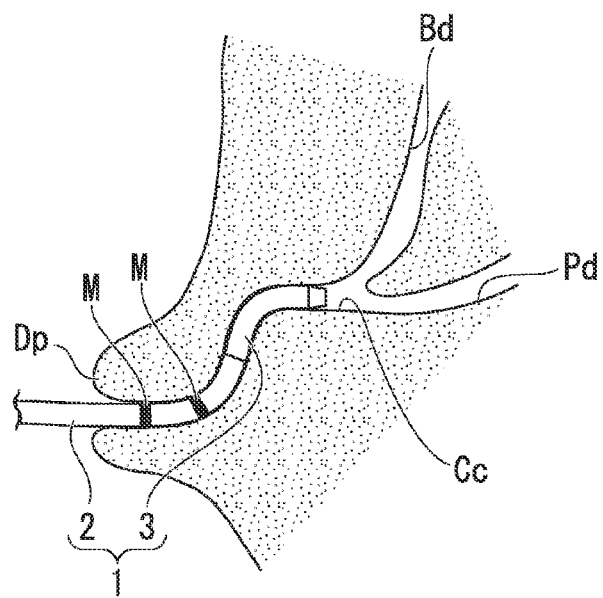
FIG. 21C is a schematic view showing one process in which the distal end of the bendable catheter in the embodiment of the present invention is inserted into the inside of a lumen tissue.

FIGS. 21A, 21B, and 21C are schematic views respectively showing one process of inserting the distal end of the bendable catheter 1 into the inside of a lumen tissue. Depending on patients, for example, as shown in FIG. 21A, the common duct Cc from the duodenal papilla Dp to a branching portion (branching portion of the bile duct Bd and the pancreatic duct Pd) may bend in the shape of a crank. In such a case, by confirming the shape of the common duct Cc by X-ray imaging and pulling the first handle 10a or the second handle 10b of the manipulating part 4 shown in FIG. 1 toward the proximal end, as shown in FIGS. 21B and 21C, the bendable part 3 can be pushed into the common duct Cc toward the deep side thereof by making the bendable part 3 run along the shape of the common duct Cc, while bending the bendable part 3 by an appropriate bending amount according to the shape of the common duct Cc.

Figure 22:
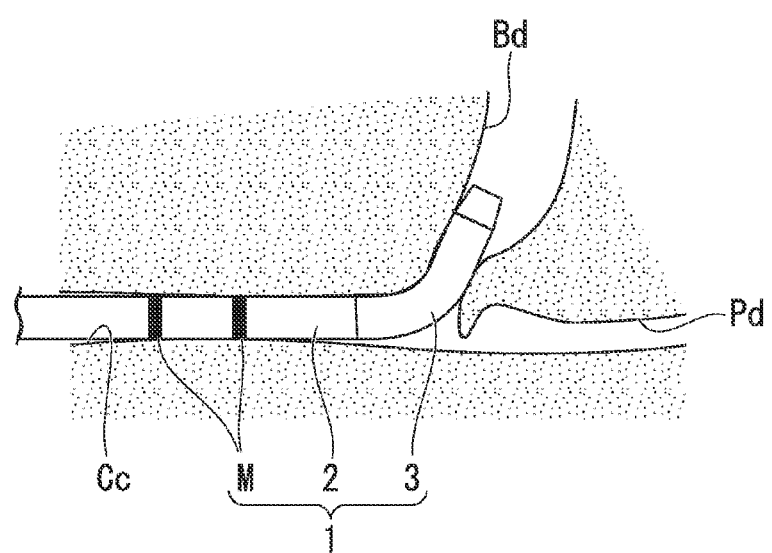
FIG. 22 is a schematic view showing one process of treatment using the bendable catheter in the embodiment of the present invention.
Figure 23:
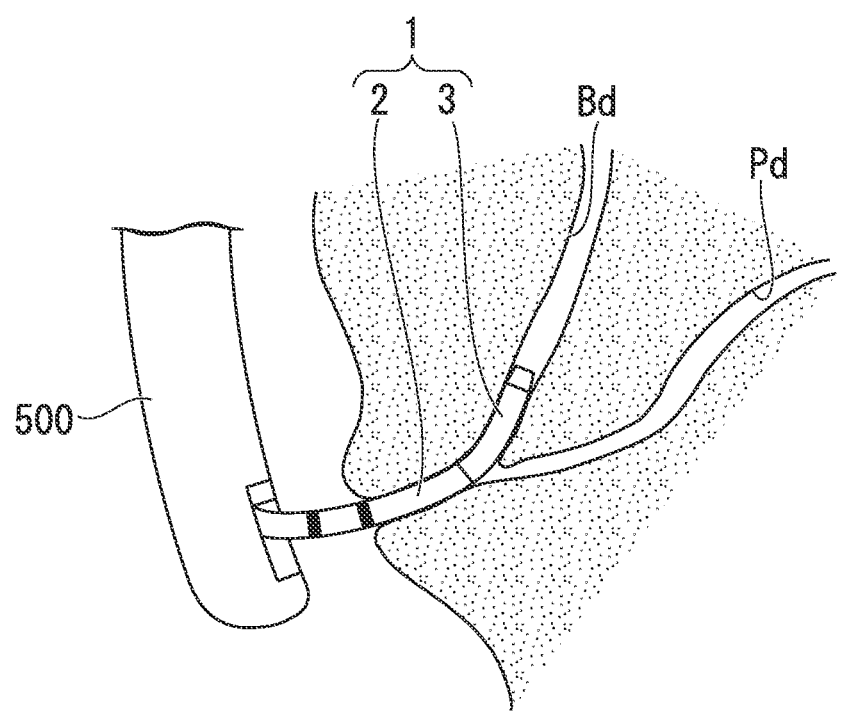
FIG. 23 is a schematic view showing one process of treatment using the bendable catheter in the embodiment of the present invention.

FIGS. 22 and 23 are schematic views showing one process of treatment using the bendable catheter 1. The manipulator further pushes the multi-lumen tube 2 into the deep side of the common duct Cc, in a state where the bendable part 3 is bent within the common duct Cc. Then, the distal end of the bendable part 3 is slidingly moved to the deep side of the common duct Cc while coming into contact with the inner wall of the common duct Cc.

The common duct Cc is branched into the bile duct Bd and the pancreatic duct Pd on the deep side of the common duct Cc. As shown in FIG. 22, if the distal end of the bendable part 3 reaches the branching portion, since the bendable part 3 is bent by an acute angle toward the bile duct Bd and the distal end of the bendable part 3 is directed toward the bile duct Bd, the bendable part 3 is easily inserted into the bile duct Bd. In addition, since the distal end of the bendable part 3 is formed in a tapered shape, even in a case where there are creases so as to plug the opening of the bile duct Bd at the branching portion on the deep side of the common duct Cc, the creases can be pushed away and the distal end of the bendable part 3 can be inserted into the inner cavity of the bile duct Bd.

As such, by pushing the multi-lumen tube 2 into the deep side of the common duct Cc from the duodenal papilla Dp in a state where the bendable part 3 is bent, the bendable part 3 is selectively inserted into the bile duct Bd.

The manipulator performs predetermined treatment on the bile duct Bd in a state where the bendable part 3 is inserted into the bile duct Bd as shown in FIG. 23. For example, a contrast medium can be injected from the port portion 13 provided in the manipulating part 4 shown in FIG. 1, and the contrast medium can be discharged from the distal end of the bendable part 3 to image the bile duct Bd.

Figure 24:
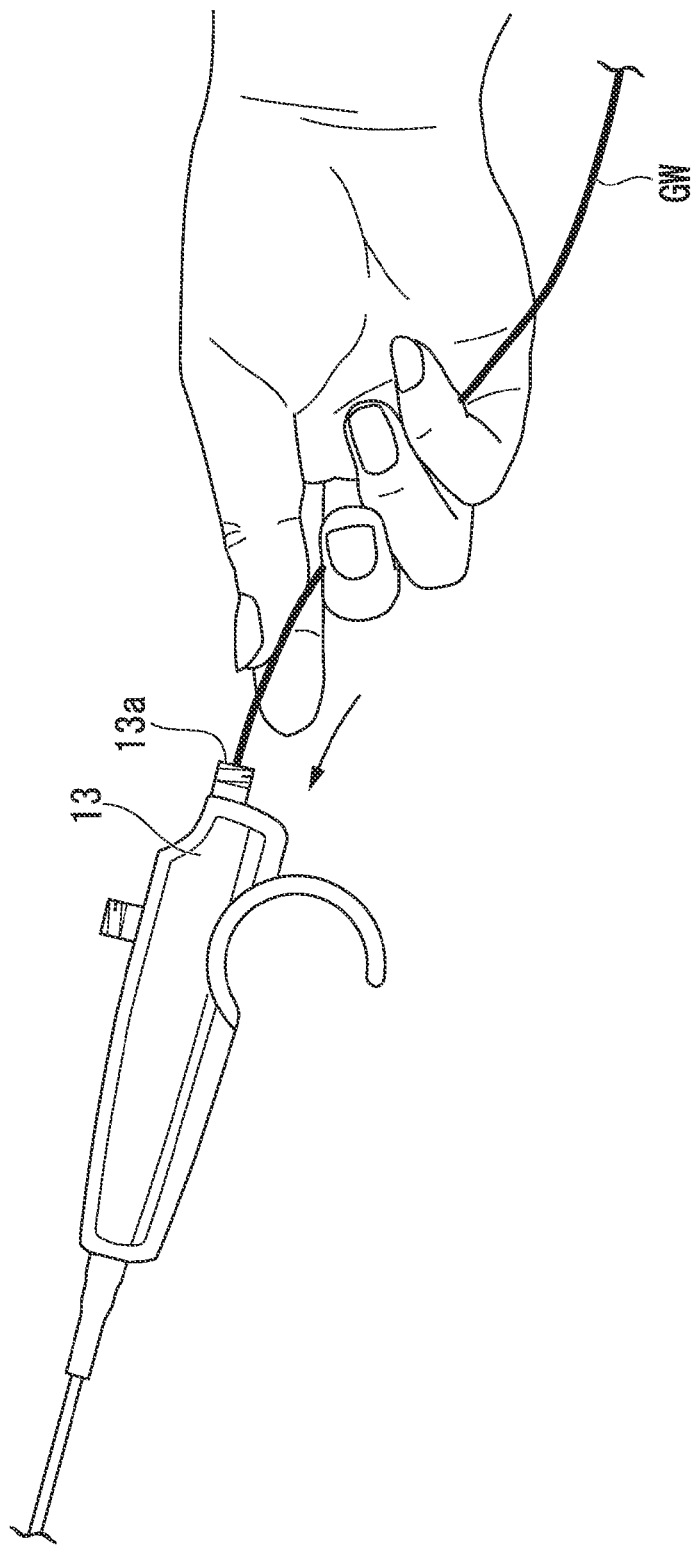
FIG. 24 is a view showing a process in which a guide wire is inserted into the bendable catheter in the embodiment of the present invention.
Figure 25:
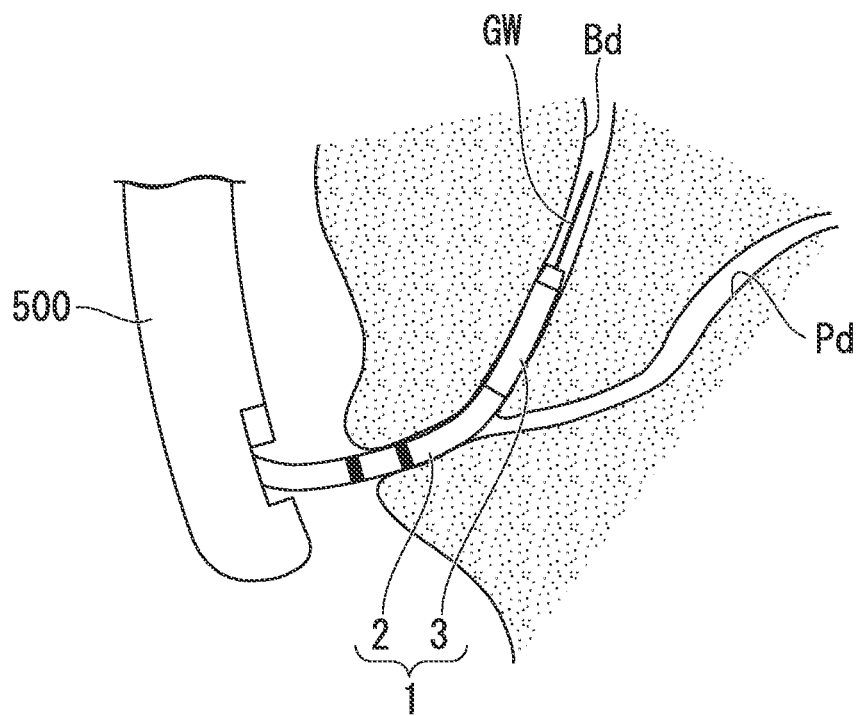
FIG. 25 is a schematic view showing one process of a procedure using the bendable catheter and the guide wire in the embodiment of the present invention.
Figure 26:
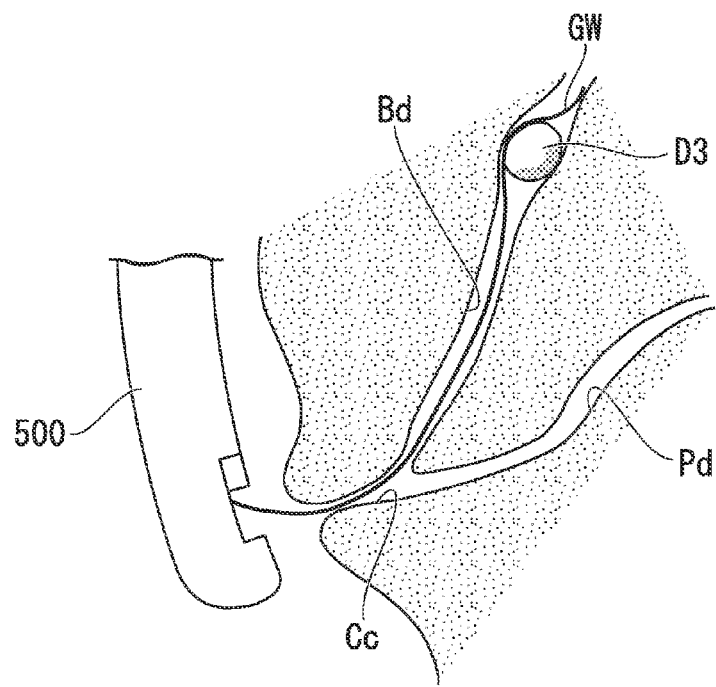
FIG. 26 is a schematic view showing one process of the procedure using the bendable catheter and the guide wire in the embodiment of the present invention.
Figure 27:
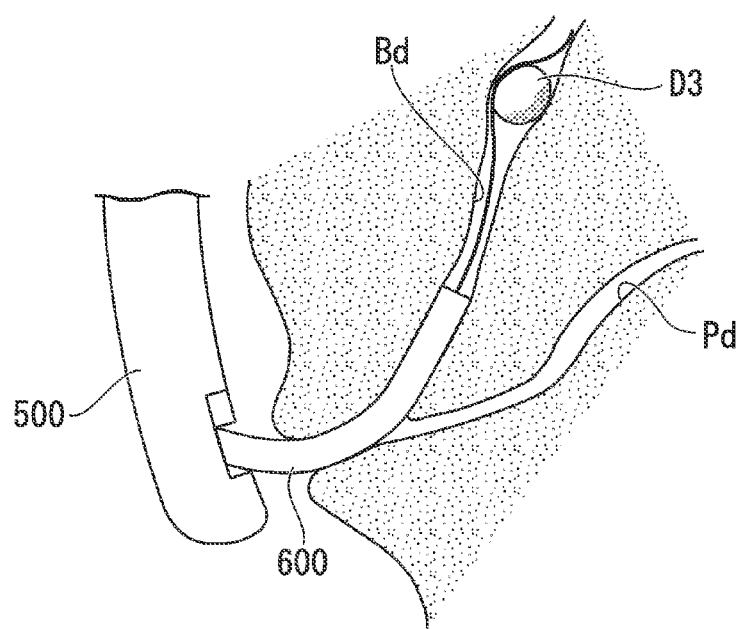
FIG. 27 is a schematic view showing one process of the procedure using the bendable catheter and the guide wire in the embodiment of the present invention.

FIG. 24 is a view showing a process in which a guide wire GW is inserted into the bendable catheter 1. FIGS. 25 to 27 are schematic views showing one process of a procedure using the bendable catheter 1 and the guide wire GW.

As shown in FIG. 24, the manipulator can insert the guide wire GW into the bendable catheter 1 by inserting the guide wire GW having flexibility from the opening portion 13a of the port portion 13.

As shown in FIG. 25, the manipulator delivers the guide wire GW from the distal end of the bendable part 3, and inserts the guide wire GW along the bile duct Bd. For example, in a case where foreign matter D3 is present inside the bile duct Bd as shown in FIG. 26, the guide wire GW is guided upstream of the foreign matter D3, and then the bendable catheter 1 is extracted from the endoscope apparatus 500, with the guide wire GW indwelled within the bile duct Bd.

Subsequently, as shown in FIG. 27, a fourth treatment tool 600 is guided along the guide wire GW, and predetermined treatment is performed on the foreign matter D3. For example, in a case where a calculus that is foreign matter within the bile duct is removed, a treatment tool for an endoscope including a crusher basket to crush the calculus can be used as the fourth treatment tool 600.

Previously, in the catheter to guide a treatment tool for an endoscope or the like to the bile duct Bd, it is difficult to enlarge the curvature when the bendable part is bent. This is because the internal space of the catheter may be plugged as the catheter having flexibility bends if an attempt to enlarge the curvature of the catheter is made. For this reason, in a case where the conventional catheter is bent largely, the guide wire GW cannot be passed therethrough, or the resistance when the guide wire GW is advanced and retracted inside the catheter may become large. Additionally, in order to make the external diameter of the catheter small while securing the space for passing the guide wire GW therethrough, it is necessary to make the thickness of the catheter small. As a result, when the catheter is bent, the catheter may be crushed more easily.

In contrast, in the bendable catheter 1 of the present usage example, the first coil 6 is provided inside the bendable part 3.

Thus, even if the bendable part 3 is bent by a large curvature, the bendable part is not easily crushed. As a result, the minimum bending radius of the bendable part 3 can be made smaller. Additionally, even in a case where the thickness of the bendable tube 5 is made small, by the installation of the first coil 6, the bendable tube 5 can be prevented from being crushed, and the bendable part 3 can be made to have a smaller diameter.

Moreover, since the minimum bending radius of the bendable part 3 can be made small, as compared to a case where bile duct insertion is performed using the conventional catheter, a procedure for aligning the orientation of the distal end of the catheter with the orientation of the bile duct Bd becomes simple. As a result, insertion into the bile duct Bd can be easily performed than ever before.

Usage Example 4

An example will be described in which a fistula (through-hole) that allows lumen tissues to communicate with each other is formed by combining the bendable catheter 1 of the present embodiment, the endoscope apparatus 500, and a fifth treatment tool inserted into the bendable catheter 1. The working and effects of the bendable catheter 1 will be described using this example.

Figure 28:
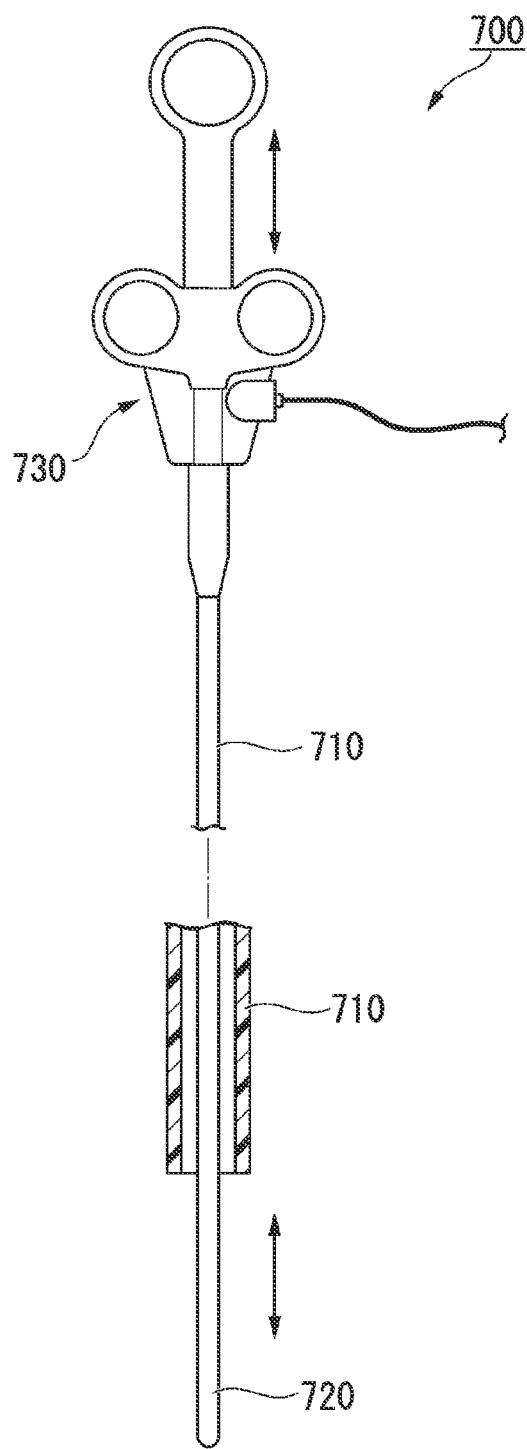
FIG. 28 is a view showing an example of a fourth treatment tool in the embodiment of the present invention.

FIG. 28 is a view showing an example of a fifth treatment tool 700 to be used along with the bendable catheter 1. As shown in FIG. 28, in the present usage example, a high-frequency knife is used as the fifth treatment tool 700 to be inserted into the bendable catheter 1. The fifth treatment tool 700 has an insertion part 710 to be inserted through the treatment tool channel 540 of the endoscope apparatus 500, a needlelike incision portion 720 provided at the distal end of the insertion part 710 to form a through-hole in a body tissue as a high-frequency current is applied thereto, and a manipulating part 730 provided at the proximal end of the insertion part 710.

Figure 29:
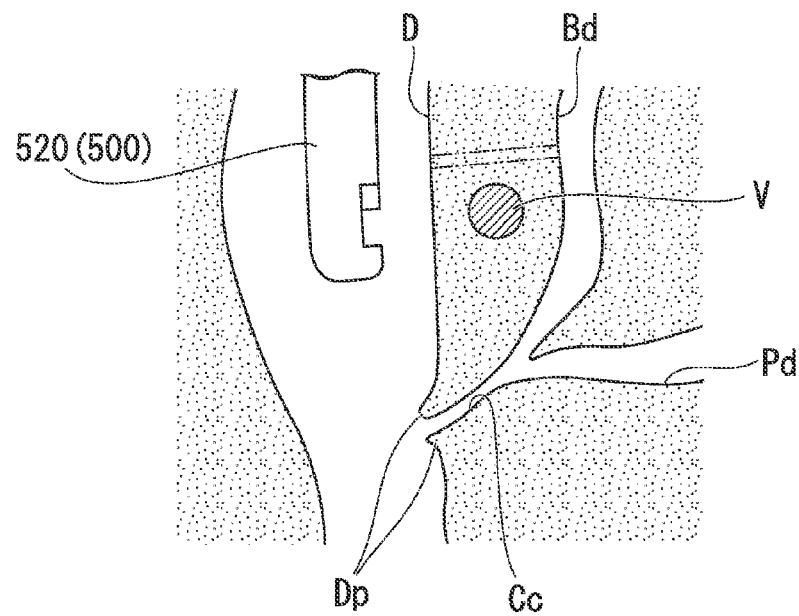
FIG. 29 is a schematic view showing one process of treatment using the bendable catheter in the embodiment of the present invention.
Figure 30:
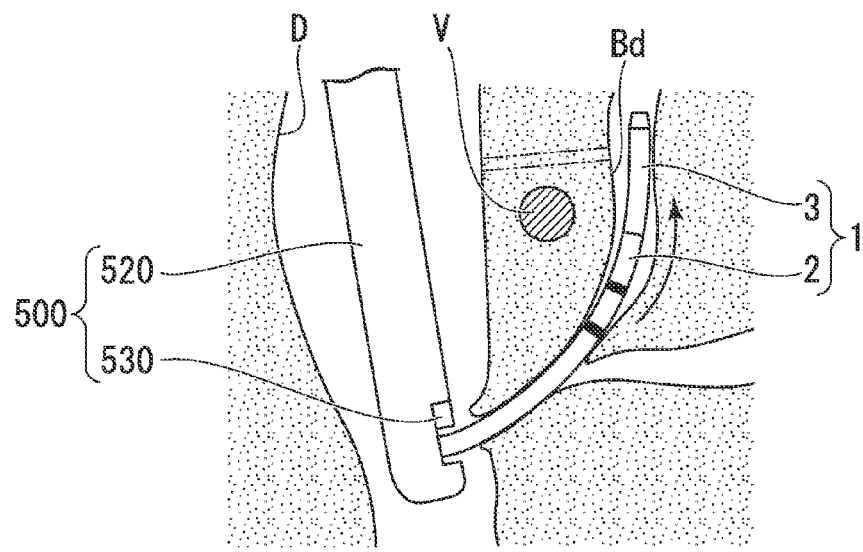
FIG. 30 is a schematic view showing one process of treatment using the bendable catheter in the embodiment of the present invention.
Figure 31:
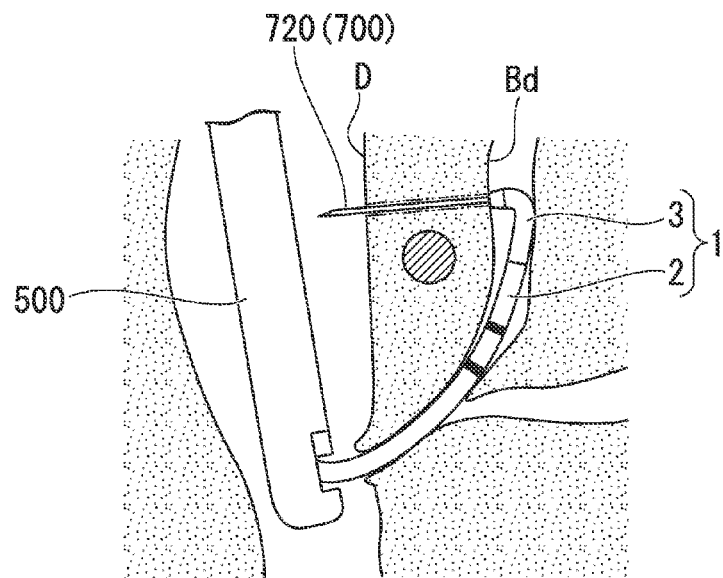
FIG. 31 is a schematic view showing one process of treatment using the bendable catheter in the embodiment of the present invention.

FIGS. 29 to 31 are schematic views showing one process of treatment using the bendable catheter 1.

In the present usage example, as shown in FIG. 29, an example of treatment that forms a fistula connecting the bile duct Bd and the duodenum D between the bile duct Bd and the duodenum D is shown.

As shown in FIG. 29, the manipulator inserts the endoscope apparatus 500 into the inside of the body cavity from a patient's natural opening, and guides the distal end of the insertion part 120 of the endoscope apparatus 500 to the vicinity of the duodenal papilla Dp. Moreover, the manipulator observes the inner wall surface of the duodenum D, and determines a suitable predetermined position in order to form a fistula. As the suitable predetermined position for forming a fistula, for example, it is preferable to select a position where a blood vessel V is avoided so that the blood vessel V or the like is not damaged.

Subsequently, as shown in FIG. 30, the manipulator captures the duodenal papilla Dp within the visual field of the imaging part 530 of the endoscope apparatus 500, and inserts the distal end of the bendable catheter 1 into the bile duct Bd similarly to the above-described Usage Example 3. The position of the bendable catheter 1 located within the bile duct Bd can be confirmed using the markings M, the first coil 6, and the second coils 7 as guides by performing X-ray imaging.

The manipulator pushes the distal end of the bendable catheter 1 to the vicinity of the predetermined position determined by observation from the duodenum D side, and bends the bendable part 3 so that the distal end of the bendable catheter 1 is directed toward the duodenum D at the predetermined position. In the present usage example, the bendable catheter 1 is arranged along the central axis of the bile duct Bd, and the manipulator bends the bendable part 3 by about 90° in order to direct the distal end of the bendable catheter 1 toward the duodenum D side.

As shown in FIG. 31, the manipulator inserts the fifth treatment tool 700 into the inside of the bendable catheter 1 from the port portion 13 of the bendable catheter 1, and makes the incision portion 720 of the fifth treatment tool 700 protrude from the distal end of the bendable part 3 of the bendable catheter 1. Then, the incision portion 720 abuts on the inner wall of the bile duct Bd. The manipulator makes a high-frequency current applied to the fifth treatment tool 700 as a high-frequency knife. Then, a body tissue contacted with the incision portion 720 to which a high-frequency current is applied is cauterized and incised, and a through-hole is formed from the bile duct Bd toward the duodenum D by the incision portion 720.

Subsequently, for example, a drainage tube or the like is attached to the through-hole, and a fistula that makes the bile duct Bd and the duodenum D communicate with each other is provided.

In the present usage example, since a through-hole is formed from the bile duct Bd with a narrower inner cavity compared to the duodenum D toward the duodenum D, an unintended through-hole can be prevented from being formed in the bile duct Bd by the distal end of the incision portion 720 as compared to a case where a through-hole is formed from the duodenum D side toward the bile duct Bd. Additionally, since a through-hole can be formed from the relatively narrower bile duct Bd toward the relatively broader duodenum D, the duodenum D and the bile duct Bd can be reliably connected together without precisely adjusting the orientation of the distal end of the incision portion 720 as compared to the case where a through-hole is formed from the duodenum D side toward the bile duct Bd.

In addition, the treatment of making blood vessels that run in parallel communicate with each other can be performed by the same procedure.

Usage Example 5

An example in which washing and suction are performed within a body cavity by the bendable catheter 1 of the present embodiment will be described. The working and effects of the bendable catheter 1 will be described using this example.

In the present usage example, an example in which washing within an abdominal cavity is performed in the operation using a laparoscope is illustrated.

Figure 32:
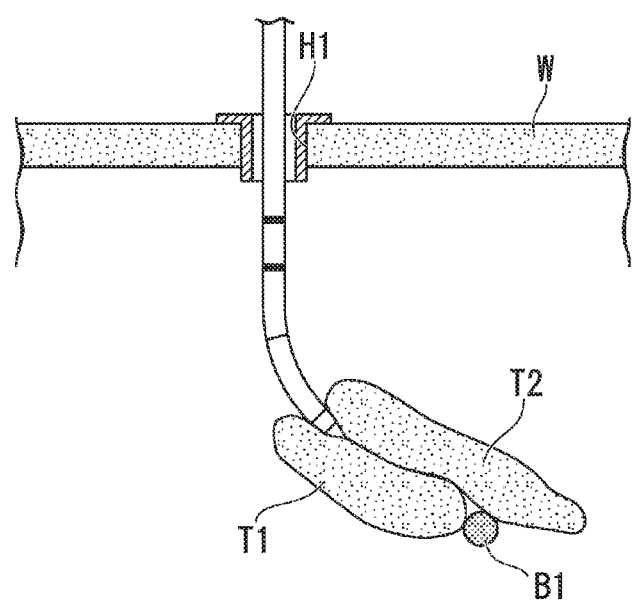
FIG. 32 is a schematic view showing one process of treatment using the bendable catheter in the embodiment of the present invention.

FIG. 32 is a schematic view showing one process of performing treatment using the bendable catheter 1 in the operation using the laparoscope.

As shown in FIG. 32, in the operation using the laparoscope, a small incision is made in the abdominal wall W so as to form a through-hole, and for example, the above-described endoscope apparatus 100 or 500 and various kinds of treatment tools are inserted into a body cavity through this through-hole. For example, in a case where treatment is performed within an abdominal cavity, a through-hole H1 through which the insertion part 120 (refer to FIG. 7) or the like of the endoscope apparatus 100 is inserted is formed in the abdominal wall W, and a trocar is attached thereto.

The manipulator introduces various kinds of treatment tools into the abdominal cavity through the through-hole H1, and performs treatment within the abdominal cavity. At this time, in a case where there is bleeding from a body tissue within the abdominal cavity, this blood stagnates within the abdominal cavity. Additionally, some blood may enter a gap between body tissues.

For example, in FIG. 32, blood B1 stagnates between two body tissues T1 and T2. In such a case, a lesion can be easily seen or treatment can be easily performed, by suctioning the blood that has entered a gap between the body tissues T1 and T2, and by washing the body tissues T1 and T2. Additionally, adhesion between internal organs within the abdominal cavity can also be prevented by washing the body tissues T1 and T2. In this case, the bendable catheter 1 is prepared in a state where a suction pump is attached to the port portion 13 formed in the manipulating part 4 of the bendable catheter 1 shown in FIG. 1.

The manipulator introduces the bendable catheter 1 into the body cavity through the through-hole H1 formed in the abdominal wall W. At this time, the position of the bendable catheter 1 within the body cavity can be confirmed using an endoscope apparatus or the like introduced into the body cavity through another through-hole. Additionally, the manipulator may insert the bendable catheter 1 through the treatment tool channel 140 of the endoscope apparatus 100 described in Usage Example 1, and may expose the distal end of the bendable catheter 1 from the distal end of the insertion part 120 of the endoscope apparatus 100 to introduce the bendable catheter 1 into the abdominal cavity.

Figure 33A:
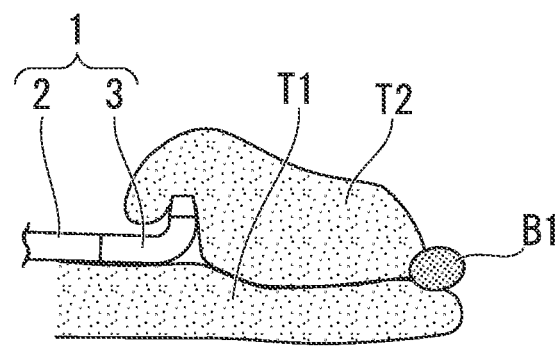
FIG. 33A is a schematic view showing another process of the treatment shown in FIG. 32.
Figure 33B:
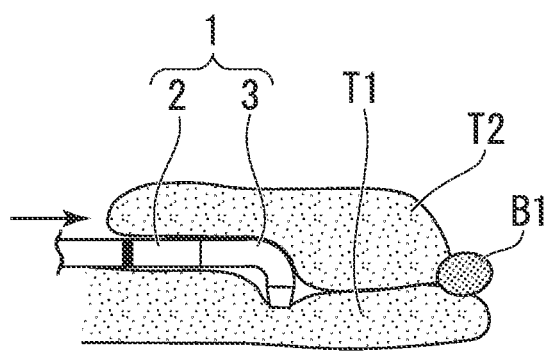
FIG. 33B is a schematic view showing another process of the treatment shown in FIG. 32.

FIGS. 33A and 33B are schematic views respectively showing another process of the treatment shown in FIG. 32. As shown in FIG. 32, the manipulator inserts the distal end of the bendable part 3 of the bendable catheter 1 into the gap between the body tissues T1 and T2. Subsequently, as shown in FIGS. 33A and 33B, the manipulator alternately pulls the first handle 10a and the second handle 10b (refer to FIG. 1) of the manipulating part 4 of the bendable catheter 1 toward the proximal end, and thereby pushes the distal end of the bendable catheter 1 between the body tissues T1 and T2 while the bendable part 3 being bent so as to alternately shake the distal end of the bendable part 3. Then, while the bendable part 3 of the bendable catheter 1 is alternately bent in opposed two directions to expand the gap between the body tissues, the bendable part 3 is pushed into the gap between the two body tissues T1 and T2.

If the distal end of the bendable part 3 has reached the position of the blood B1, the suction pump connected to the port portion 13 is operated. Then, the blood B1 is suctioned through the inside of the bendable part 3 and the first lumen 2c (refer to FIG. 3) from the distal end of the bendable part 3, and is discharged to the outside of the body.

In the present usage example, the bendable catheter 1 can be inserted into the gap between body tissues by alternately bending the bendable part 3 of the bendable catheter 1, without separately using a retractor to move the body tissues within the body cavity. For this reason, it becomes unnecessary to further incise the abdominal wall W in order to insert the retractor into the body cavity, and invasion to a patient can be reduced.

In addition, the procedure described in the present usage example can also be applied to a case where an exudation liquid is discharged or a cell sample is taken from ascites or pleural effusions other than the case where blood is discharged.

Usage Example 6

An example will be described in which the inside of a body cavity is observed by combining the bendable catheter 1 of the present embodiment, the endoscope apparatus 100, and the fifth treatment tool 700 and an inside-of-body observation device (not shown) to be inserted into the bendable catheter 1. The working and effects of the bendable catheter 1 will be described using this example.

In the present usage example, the endoscope apparatus 100 of the same type as the above-described Usage Example 1 is used, a through-hole is formed in a stomach wall, and the inside of an abdominal cavity is observed by passing the above inside-of-body observation device through this through-hole. The inside of the abdominal cavity can be observed in such a procedure without small incision in the abdominal wall.

Additionally, the inside-of-body observation device to be inserted into the bendable catheter 1 in the present usage example includes an imaging part at a distal end thereof, and the inside of the body can be observed by this imaging part.

Figure 34:
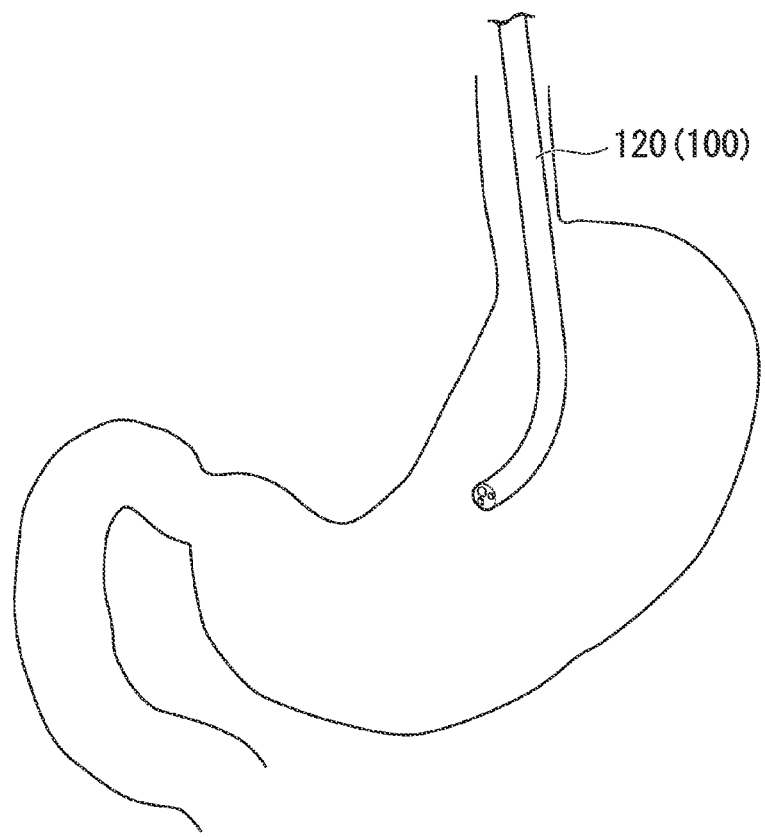
FIG. 34 is a schematic view showing one process of treatment using the bendable catheter in the embodiment of the present invention.
Figure 35:
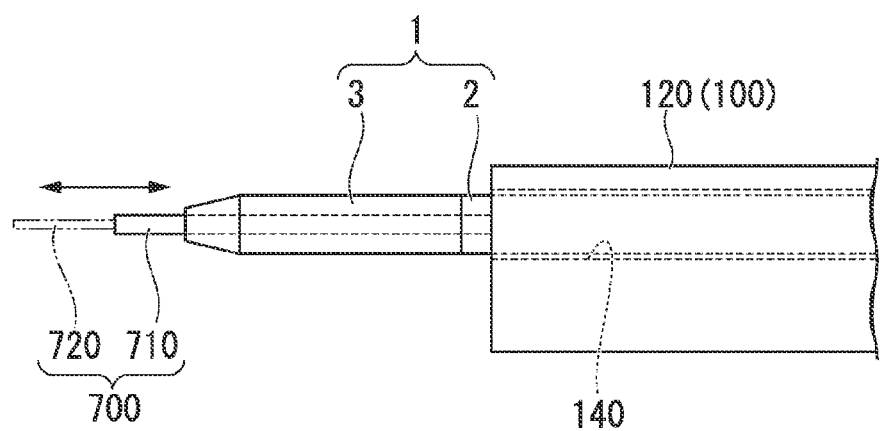
FIG. 35 is a schematic view showing one process of treatment using the bendable catheter in the embodiment of the present invention.

FIGS. 34 and 35 are schematic views showing one process of treatment using the bendable catheter 1.

As shown in FIG. 34, in the present usage example, first, the insertion part 120 of the endoscope apparatus 100 is inserted into a patient's body from a patient's mouth, and the distal end of the insertion part 120 is guided into a patient's stomach.

Subsequently, the fifth treatment tool 700 is inserted into the bendable catheter 1 through the port portion 13, and the distal end of the bendable catheter 1 is made to protrude from the distal end of the treatment tool channel 140 of the endoscope apparatus 100 (refer to FIG. 35).

Figure 36:
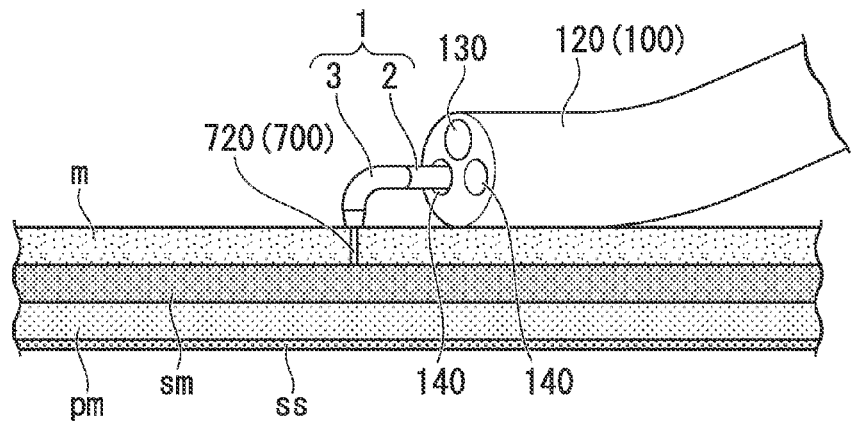
FIG. 36 is a schematic view showing a process in which a layer of the stomach wall is incised using the bendable catheter in the embodiment of the present invention.
Figure 37A:
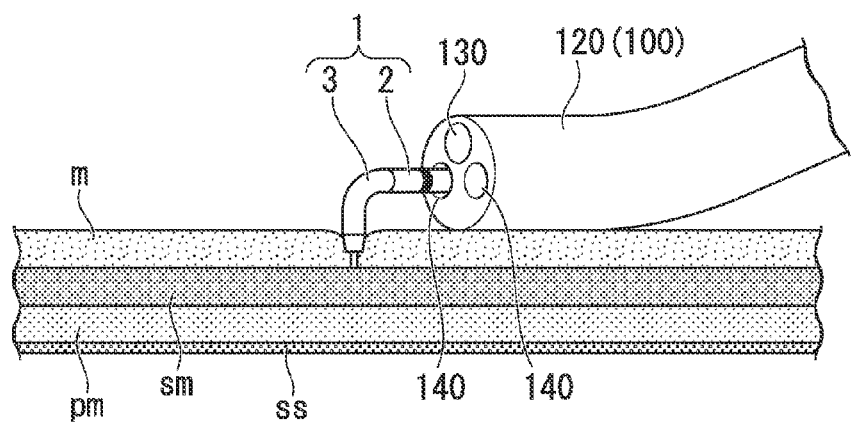
FIG. 37A is a schematic view showing a process in which the bendable catheter in the embodiment of the present invention is inserted into the layer of the stomach wall.
Figure 37B:
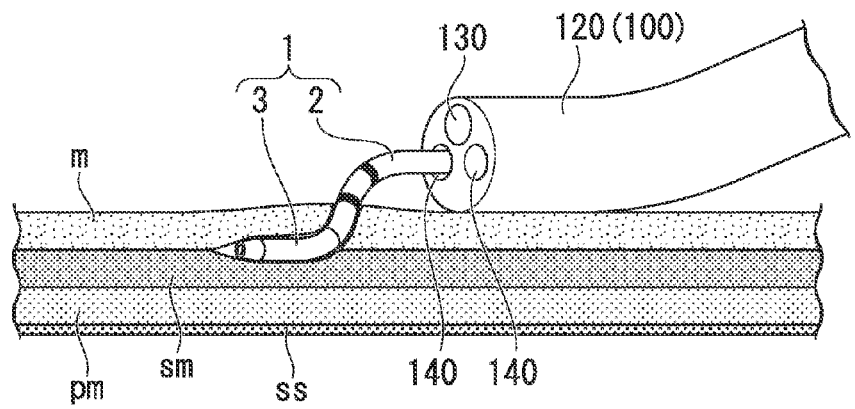
FIG. 37B is a schematic view showing a process in which the bendable catheter in the embodiment of the present invention is inserted between layers of the stomach wall.
Figure 38:
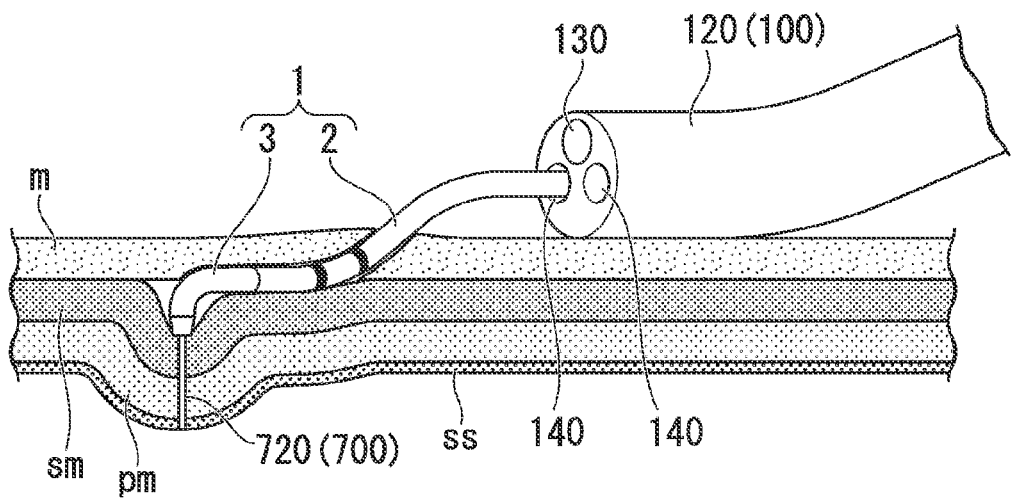
FIG. 38 is a schematic view showing a process in which a through-hole is formed in some layers of the stomach wall using the bendable catheter in the embodiment of the present invention.
Figure 39:
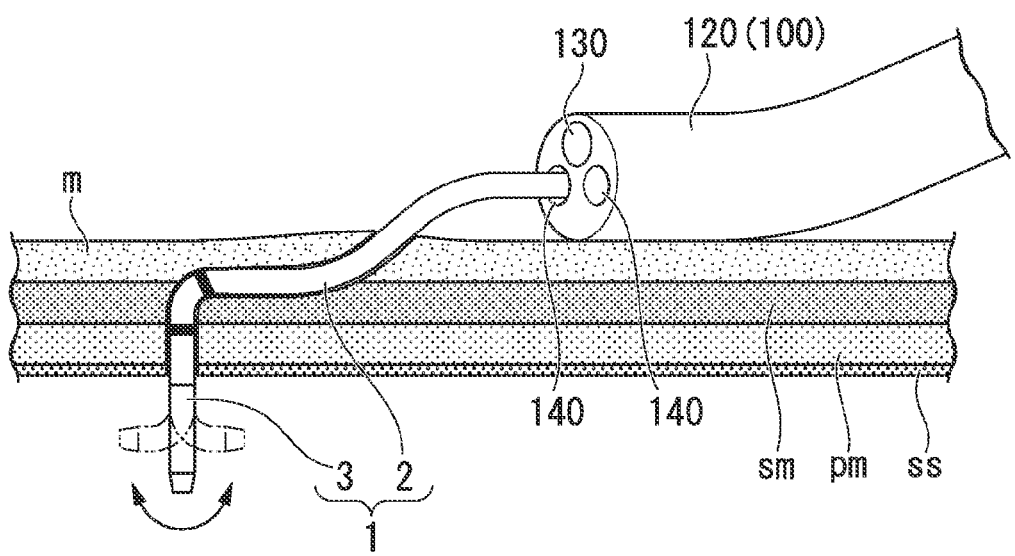
FIG. 39 is a schematic view showing a process in which the inside of an abdominal cavity is observed using the bendable catheter in the embodiment of the present invention.

FIG. 36 is a schematic view showing a process in which a layer of the stomach wall is incised using the bendable catheter 1. FIG. 37A is a schematic view showing a process in which the bendable catheter 1 is inserted into the layer of the stomach wall. FIG. 37B is a schematic view showing a process in which the bendable catheter 1 is inserted between layers of the stomach wall. FIG. 38 is a schematic view showing a process in which a through-hole is formed in some layers of the stomach wall. FIG. 39 is a schematic view showing a process in which the inside of the abdominal cavity is observed using the bendable catheter 1 inserted through the through-hole formed in the stomach wall.

As shown in FIG. 36, the manipulator incises a mucosal layer m of the stomach using the fifth treatment tool 700, and exposes a submucosal layer sm.

Subsequently, as shown in FIG. 37A, the distal end of the bendable catheter 1 is inserted between the mucosal layer m and the submucosal layer sm of the stomach, and the bendable catheter 1 is pushed in between the mucosal layer m and the submucosal layer sm while peeling off the mucosal layer m and the submucosal layer sm as shown in FIG. 37B.

Subsequently, as shown in FIG. 38, the manipulator moves the distal end of the bendable catheter 1 to a position apart from the position where the mucosal layer m is incised, between the mucosal layer m and the submucosal layer sm. The manipulator pulls the first handle 10a or the second handle 10b of the manipulating part 4 toward the proximal end, and bends the bendable part 3 of the bendable catheter 1. In the present usage example, the bendable catheter 1 is arranged along the submucosal layer sm. Thus, in order to make a through-hole in the submucosal layer sm, a muscular layer pm, and a serous membrane ss, the bendable part 3 is bent by 90° from a linear state so as to direct the distal end of the bendable part 3 toward the submucosal layer sm, the muscular layer pm, and the serous membrane ss.

The manipulator pushes the distal end of the incision portion 720 of the fifth treatment tool 700 against the submucosal layer sm, and applies a high-frequency current to the incision portion 720. Then, the submucosal layer sm with which the incision portion 720 comes into contact is cauterized and incised, and a through-hole is formed in the submucosal layer sm. Moreover, the through-hole is also formed similarly in the muscular layer pm and the serous membrane ss that overlap the submucosal layer sm. This enables a tunnel allowing the inside of the stomach and the inside of the abdominal cavity to communicate with each other to be formed within the stomach wall. The manipulator inserts the distal end of the bendable part 3 into the through-hole formed in the submucosal layer sm, the muscular layer pm, and the serous membrane ss, and guides the bendable part 3 into the abdominal cavity.

As shown in FIG. 39, the manipulator extracts the fifth treatment tool 700 from the bendable catheter 1, inserts the above-described inside-of-body observation device to image the inside of the abdominal cavity through the bendable catheter 1, and observes the inside of the abdominal cavity. In addition, as the inside-of-body observation device, a device that acquires an optical image, a device that radiates ultrasonic waves to generate an image, or the like can be used appropriately.

Figure 40:
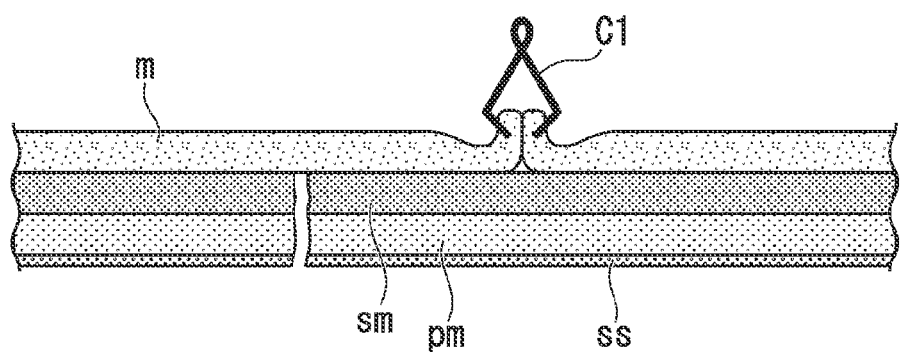
FIG. 40 is a schematic view showing a state where the through-hole formed in the stomach wall is closed.

FIG. 40 is a schematic view showing a state where the through-hole formed in the stomach wall is closed.

If the observation within the abdominal cavity is completed as shown in FIG. 40, the bendable catheter 1 is pulled back into the stomach, and then the incised portion of the mucosal layer m is sutured by a clip C1 or the like, and the treatment is ended.

In addition, if other treatment is required within the abdominal cavity, the through-hole formed using the bendable catheter 1 is expanded, or another through-hole is formed in the stomach wall after the bendable catheter 1 is pulled back into the stomach and the incised portion of the mucosal layer m is sutured by a clip or the like. Thereby, required treatment is performed within the abdominal cavity using the endoscope apparatus 100 and other treatment tools to be used for treatment within the abdominal cavity.

In the present usage example, the position where incision is made on the mucosal layer m, and the position where the through-hole is formed in the submucosal layer sm, the muscular layer pm, and the serous membrane ss are different positions as seen from the thickness direction of the stomach wall. For this reason, the possibility that infection may be caused from the inside of the stomach into the abdominal cavity through these through-holes after the incised portion formed in the gastric mucous membrane is sutured can be reduced.

In addition, previously, the mucosal layer m is peeled off and turned over in order to form a tunnel between the mucosal layer m and the submucosal layer sm. In contrast, in the present usage example, the bendable catheter 1 is just inserted between the mucosal layer m and the submucosal layer sm. Thus, the area of the mucosal layer m to be peeled off can be made small, and invasion to a patient can be reduced further.

In addition, even in a case of the treatment of indwelling a marker in a tissue within an abdominal cavity or indwelling an indwelling type electrode in a tissue within an abdominal cavity, the treatment can be performed by the same procedure as the present usage example.

(Modification)

Next, a modification of the bendable catheter 1 described in the above-described embodiment will be described.

Figure 41:
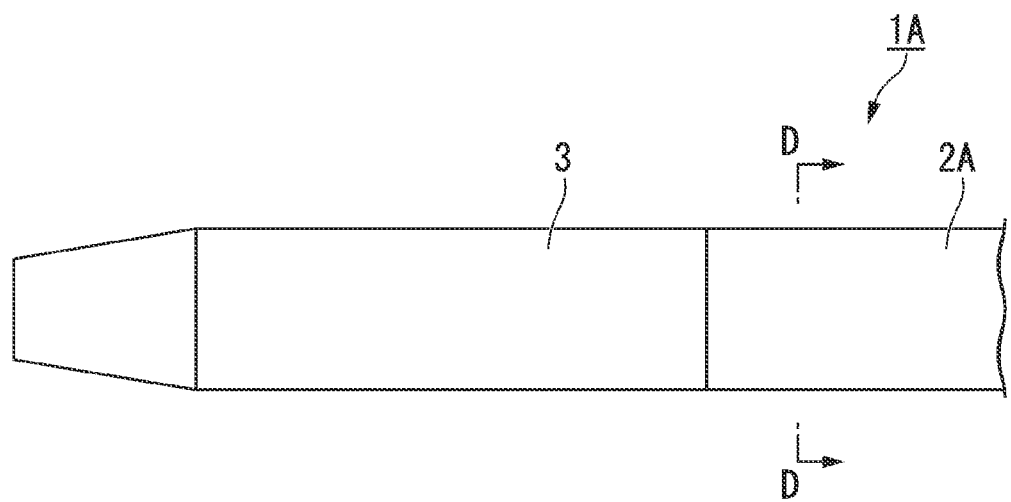
FIG. 41 is a view showing a modification of the bendable catheter in the embodiment of the present invention.
Figure 42:
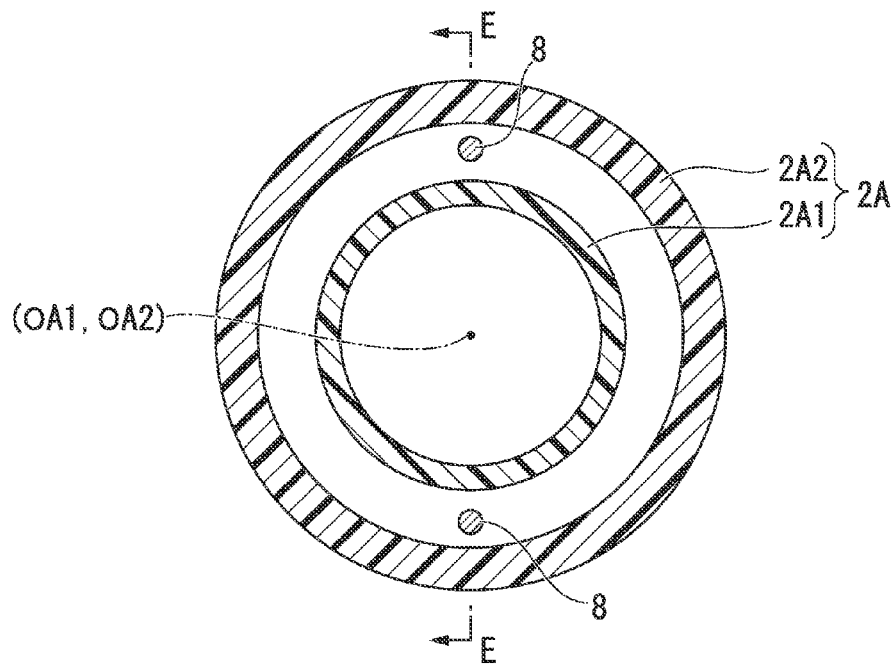
FIG. 42 is a cross-sectional view in a line D-D of FIG. 41.
Figure 43:
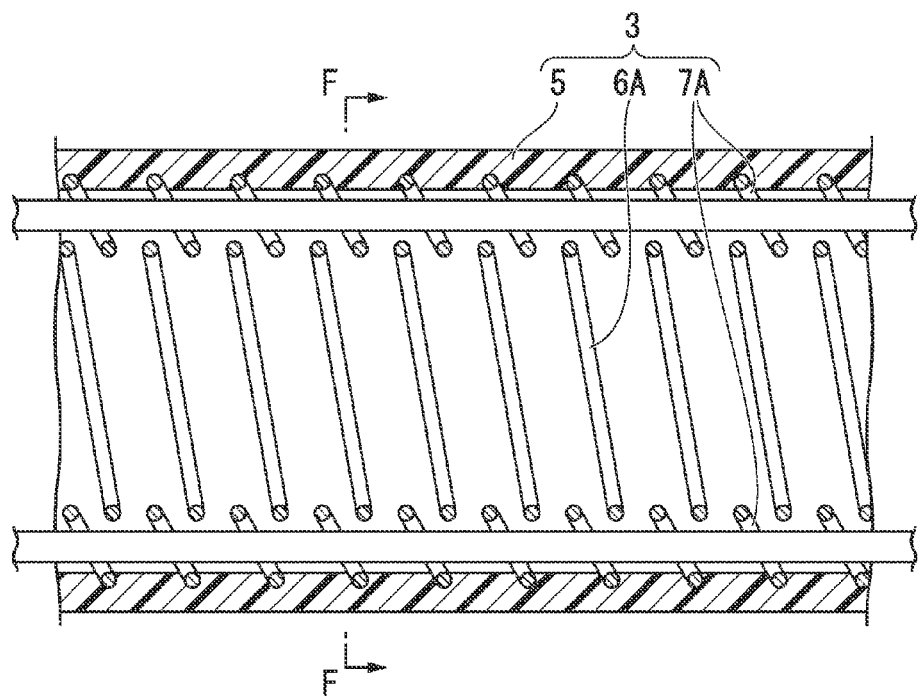
FIG. 43 is a cross-sectional view as a bendable part of the bendable catheter shown in FIG. 41 is seen in a section in a line E-E of FIG. 42.
Figure 44:
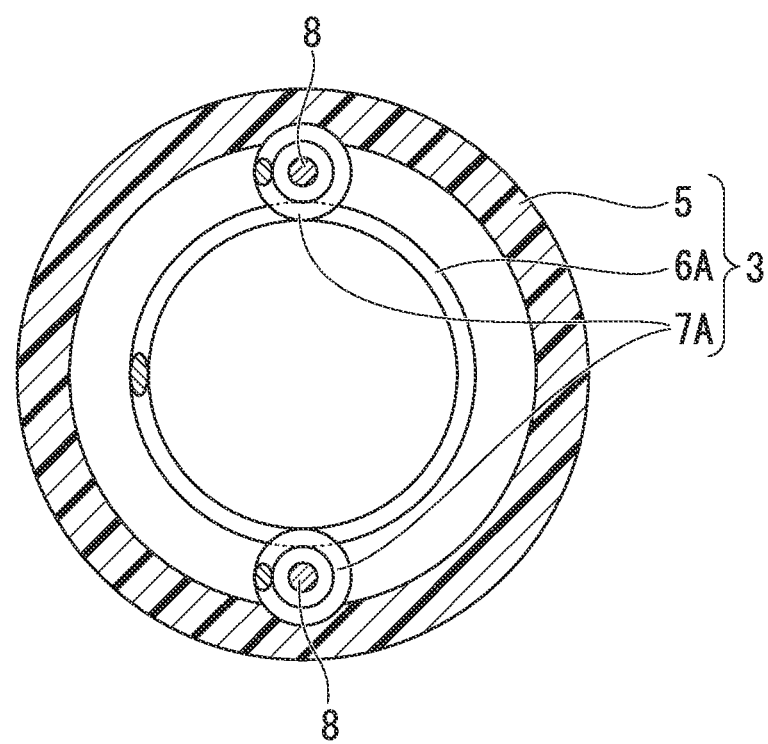
FIG. 44 is a cross-sectional view in a line F-F of FIG. 43.

FIG. 41 is a view showing a bendable catheter 1A of the present modification. FIG. 42 is a cross-sectional view in a line D-D of FIG. 41. FIG. 43 is a cross-sectional view as the bendable part of the bendable catheter shown in FIG. 41 is seen in a section in a line E-E of FIG. 42. FIG. 44 is a cross-sectional view in a line F-F of FIG. 43.

As shown in FIGS. 41 and 42, the bendable catheter 1A of the present modification is different from the above-described bendable catheter 1 in terms of including a flexible tubular main tube 2A instead of the multi-lumen tube 2 and the configuration of the bendable part 3.

As shown in FIG. 42, the main tube 2A includes a first tube 2A1, and a second tube 2A2 through which the first tube 2A1 is inserted. The first tube 2A1 is a tubular member having a central axis OA2 on the same axis as a central axis OA of the main tube 2A. The internal space of the first tube 2A1, similarly to the first lumen 2c described in the above-described embodiment, is used to allow a medical treatment tool or a guide wire to be inserted therethrough or to perform air supply, water supply, or suction.

The external diameter of the first tube 2A1 is smaller than the internal diameter of the second tube 2A2, and a gap is present between the first tube 2A1 and the second tube 2A2. In the present modification, the bending manipulation wires 8 are inserted between the first tube 2A1 and the second tube 2A2, and the space between the first tube 2A1 and the second tube 2A2 becomes a lumen equivalent to the second lumens 2d described in the above-described embodiment.

The materials of the first tube 2A1 and the second tube 2A2 can be the same material as the material of the above-described multi-lumen tube 2. Additionally, the material of the first tube 2A1 and the material of the second tube 2A2 may be the same, or may be different from each other.

Additionally, as shown in FIG. 43, the bendable part 3 in the present modification includes a first coil 6A instead of the first coil 6, and includes second coils 7A instead of the second coils 7.

The first coil 6A is a cylindrical coil formed of a metal wire rod similarly to the above-described first coil 6. The first coil 6A is a loosely wound coil, and the size of a gap between adjacent metal wire rods of the first coil 6A is larger than the diameter of the metal wire rod of the second coil 7A to be described below.

The second coil 7A is a cylindrical coil formed of a metal wire rod similarly to the above-described first coil 6A. The winding interval of the second coil 7A is equal to the winding interval of the first coil 6A. As seen from a direction orthogonal to the central axis of the first coil 6A, the positional relationship between the second coils 7A and the first coil 6A is the positional relationship in which a part of the metal wire rod of the second coil 7A has entered the gap between the adjacent metal wire rods of the first coil 6A.

In a portion in which the part of the metal wire rod of the second coil 7A that has entered the gap between the adjacent metal wire rods of the first coil 6A, the metal wire rod of the first coil 6A and the metal wire rod of the second coil 7A are arranged alternately in the direction of the central axis of the second coil 7A.

As shown in FIG. 44, as seen from the direction of the central axis of the second coil 7A, the outer peripheral portion of the first coil 6A and the inner peripheral portion of the second coil 7A are in contact with each other, and the inner peripheral portion of the first coil 6A and the outer peripheral portion of the second coil 7A are in contact with each other. The second coil 7A does not protrude further inward than the inner peripheral portion of the first coil 6A, and the first coil 6A does not protrude further inward than the inner peripheral portion of the second coil 7A. For this reason, the internal space of the first coil 6A is columnar, and the internal space of each second coil 7A is also columnar.

In the present modification, since the main tube 2A is configured by combining the first tube 2A1 and the second tube 2A2 with simple tubular shapes, the main tube 2A can be manufactured easily.

Moreover, in the present modification, the positional relationship in which a part of the metal wire rod of the second coil 7A has entered the gap between the adjacent metal wire rods of the first coil 6A is satisfied. Thus, the bendable part 3 can be made to have a smaller diameter than the configuration described in the above-described embodiment.

Although the preferable embodiment of the present invention has been described hitherto, the present invention is not limited to the embodiment. Additions, omissions, substitutions, and other modifications can be made without departing from the concept of the present invention.

For example, in order to reduce friction against the manipulating part 4, the main tube 2A, and the second coils 7 and 7A, coatings using fluororesins, such as PTFE, may be provided on the external surfaces of the bending manipulation wires 8.

Additionally, in addition to the distal end 7a of the second coil 7, the distal end 8a of the bending manipulation wire 8 may also be fixed to the distal end 6a of the first coil 6, for example by brazing, soldering, or welding. In this case, the first coil 6, the second coils 7, and the bending manipulation wires 8 are fixed integrally in a process before being attached to the multi-lumen tube 2 or the main tube 2A, and the bendable tube 5. This enables the first coil 6, the second coils 7, and the bending manipulation wires 8 to be easily attached to the multi-lumen tube 2 or the main tube 2A, and the bendable tube 5.

Additionally, the distal end 8a of the bending manipulation wire 8 may be heat-welded or bonded to the inner wall surface at the distal end of the bendable tube 5.

Additionally, the distal end 8a of the bending manipulation wire 8 may be fixed to the distal end of the first coil 6 instead of being fixed to the second coil 7.

In addition, the present invention is not limited by the above description and is limited by only the scope of the appended claims.

According to the present invention, the inner cavity of the bendable catheter can be prevented from being plugged even if the bendable catheter is bent largely. Therefore, the bendable catheter can be bent largely compared to the conventional catheter.

Since the bendable catheter is bent largely, the bendable catheter can be suitably and easily inserted into a thin body cavity or into a body cavity that branches at the middle thereof.

Additionally, even in a case where a treatment tool for incision is inserted through the bendable catheter and the treatment of excising a lesion is performed, the distal end of the treatment tool for incision can be precisely directed to the lesion because the bendable catheter can bend largely. Hence, the lesion can be suitably excised with easy manipulation, while preventing a body tissue around the lesion from being damaged.

The invention claimed is:
1. A bendable catheter comprising:
a main tube comprising a distal end, a proximal end, and a first lumen and a second lumen that communicate from the distal end to the proximal end, wherein the first lumen is parallel with the second lumen;
a bendable part having a longitudinal axis and including a first internal space formed along the longitudinal axis, wherein the bendable part is provided at the distal end of the main tube and is capable of being bent;

a first coil including a second internal space formed along the longitudinal axis, wherein the first coil is fixed with a distal end of the first lumen at a position where the second internal space is communicated with the first lumen, and wherein the first coil extends to a distal end of the bendable part in the first internal space;

a second coil including a third internal space formed along the longitudinal axis, wherein the second coil is fixed with a distal end of the second lumen at a position where the third internal space is communicated with the second lumen, wherein the second coil extends to the distal end of the bendable part in the first internal space, and wherein the second coil is arranged parallel with the first coil between the bendable part and the first coil in the longitudinal axis; and a bending manipulation wire inserted through the third internal space and the second lumen, wherein the bending manipulation wire is arranged so as to be movable along the longitudinal axis within the second coil, and wherein a distal end of the bending manipulation wire is fixed to the bendable part to cause the bendable part to bend in accordance with movement of the bending manipulation wire in a direction of the longitudinal axis, wherein the bendable part comprises a bendable tube fixed to the distal end of the main tube, and wherein the second coil is fixed in the distal end of the main tube.

2. The bendable catheter according to claim 1, wherein the bendable tube is more flexible than the main tube.

3. The bendable catheter according to claim 2, wherein a proximal end of the second coil is closer to a distal end of the bendable catheter than an opening at the distal end in the first lumen, and the first coil is fixed to an inner wall surface of the first lumen.

4. The bendable catheter according to claim 2, wherein the first coil has a space between the turns thereof, and the second coil has a space between the turns thereof.

5. The bendable catheter according to claim 2, wherein the main tube and the bendable tube have light permeability.

6. The bendable catheter according to claim 2, wherein the main tube includes:

a first tubular tube fixed to a proximal end of the first coil and having the first lumen formed therein; and a second tubular tube through which the first tube inserted and having the second lumen between the first tube and the second tube.

7. The bendable catheter according to claim 2, wherein the first coil has a length in a direction of the central axis thereof longer than the second coil.

8. The bendable catheter according to claim 2, wherein the second coil is exposed inside the bendable tube.

9. The bendable catheter according to claim 2, wherein an external surface of the second coil is in contact with an external surface of the first coil.

10. The bendable catheter according to claim 2, wherein each loop of the second coil enters between adjacent loops of the first coil, and a wire of the first coil and a wire of the second coil are arranged alternately in a direction of the central axis of the first coil, in a portion where the second coil enters the first coil.

11. The bendable catheter according to claim 2, wherein a winding interval of a wire of the first coil and a winding interval of a wire of the second coil are equal to each other.

12. The bendable catheter according to claim 2, wherein at least one of the first coil and the second coil contains a material which appears on an X-ray transparent image.

13. The bendable catheter according to claim 2, wherein a distal end of the first coil and a distal end of the second coil are fixed together by brazing, soldering, or welding.

14. The bendable catheter according to claim 2, wherein a distal end of the second coil and a distal end of the bending manipulation wire are fixed together by brazing, soldering, or welding.

15. The bendable catheter according to claim 1, wherein a pair of second coils is provided so as to sandwich the first coil.

16. The bendable catheter according to claim 1, wherein an external diameter of the first coil is larger than an external diameter of the second coil.

* * * * *